US005936716A

United States Patent [19]
Pinsukanjana et al.

[11] Patent Number: 5,936,716
[45] Date of Patent: *Aug. 10, 1999

[54] METHOD OF CONTROLLING MULTI-SPECIES EPITAXIAL DEPOSITION

[76] Inventors: Paul Ruengrit Pinsukanjana, 45 South Avon St. #20A, St. Paul, Minn. 55105; Arthur Charles Gossard, 4250 Via Esperanza, Santa Barbara, Calif. 93110; Andrew William Jackson, 1972 Las Canoas Rd., Santa Barbara, Calif. 93105; Jan Arild Tofte, 775 Camino Del Sur, Apt. A12, Goleta, Calif. 93117; John H. English, 1331 Willow St., Santa Ynez, Calif. 93460

[ * ] Notice: This patent is subject to a terminal disclaimer.

[21] Appl. No.: 08/807,663

[22] Filed: Feb. 27, 1997

Related U.S. Application Data

[63] Continuation-in-part of application No. 08/657,614, May 31, 1996.
[51] Int. Cl.$^6$ ........................................................ G01N 21/31
[52] U.S. Cl. ............................... 356/72; 356/311; 117/86; 117/202
[58] Field of Search ............................... 356/72, 311, 316; 117/85, 86, 201, 202

[56] References Cited

U.S. PATENT DOCUMENTS

| | | |
|---|---|---|
| 3,654,109 | 4/1972 | Hohl et al. ............................... 250/343 |
| 3,865,625 | 2/1975 | Yi Cho et al. . |
| 4,300,833 | 11/1981 | Harnly et al. . |
| 4,815,848 | 3/1989 | Hadeishi . |
| 4,822,168 | 4/1989 | Nogami et al. . |
| 4,945,254 | 7/1990 | Robbins . |
| 5,038,038 | 8/1991 | Weniger et al. . |
| 5,066,124 | 11/1991 | Wulf . |
| 5,171,399 | 12/1992 | Brennan et al. . |
| 5,254,207 | 10/1993 | Nishizawa et al. . |
| 5,364,492 | 11/1994 | Eckstein et al. . |
| 5,399,521 | 3/1995 | Celii et al. . |
| 5,400,739 | 3/1995 | Kao et al. . |

OTHER PUBLICATIONS

T.Y. Kometani and W. Wiegmann, "Measurements of Ga and Al in a Molecular–beam Epitaxy Chamber by Atomic Absorption Spectrometry (AAS)," *J. Vac. Sci. Technol.*, vol. 12, No. 4, Jul./Aug. 1995, 933–936.

M.E. Klausmeier–Brown, J.E. Eckstein, I. Bozovic, and G.F. Virshup, "Accurate Measurement of Atomic Beam Flux by Pseudo–double–beam Atomic Absorption Spectroscopy for Growth of Thin–film Oxide Superconductors," *Appl. Phys. Lett.*, vol. 60, No. 5, Feb. 3, 1992, 657–659.

S.A. Chalmers and K.P. Killeen, "Real–time Control of Molecular Beam Epitaxy by Optical–based Flux Monitoring," *Appl. Phys. Lett.*, vol. 63, No. 23, Dec. 6, 1993, 3131–3133.

S.A. Chalmers, K.P. Killeen and E.D. Jones, "Accurate Multiple–quantum–well Growth Using Real–time Optical Flux Monitoring," *Appl. Phys. Lett.*, vol. 65, No. 1, Jul. 4, 1994, 4–6.

S.J. Benerofe, C.H. Ahn, M.M. Wang, K.E. Kihlstrom, K.B. Do, S.B. Arnason, M.M. Fejer, T.H. Geballe, M.R. Beasley and R.H. Hammond, "Dual Beam Atomic Absorption Spectroscopy for Controlling Thin Film Deposition Rates," *J. Vac. Sci. Technol. B*, vol. 12, No. 2, Mar./Apr. 1994, 1217–1220.

(List continued on next page.)

*Primary Examiner*—F. L. Evans
*Attorney, Agent, or Firm*—Merchant, Gould, Smith, Edell, Welter & Schmidt

[57] ABSTRACT

An integrated dual beam multi-channel optical-based flux monitor and method of monitoring atomic absorption of a plurality of atomic species during epitaxial deposition. Light from multiple sources is simultaneously passed through a region of deposition of material such that atomic absorption takes place. The light that passed through the region is then compared to light in a reference arm that did not pass through a region of atomic absorption. From this comparison the deposition of an epitaxial layer can be carefully monitored and controlled.

59 Claims, 23 Drawing Sheets

OTHER PUBLICATIONS

C. Lu and Y. Guan, "Improved Method of Nonintrusive Deposition Rate Monitoring by Atomic Absorption Spectroscopy for Physical Vapor Deposition Processes," *J. Vac. Sci. Technol. A*, vol. 13, No. 3, May/Jun. 1995, 1797–1801.

Brochure, "ATOMICAS A New Breakthrough in Thin Film Deposition Rate Monitoring Technology," Intelligent Sensor Technology, Inc., Mountain View, CA, Oct. 1994, 4 pages.

Weizhi Wang, R. H. Hammond, M. M. Fejer, C. H. Ahn and M.R. Beasely; M.D. Levenson and M. L. Bortz, "Diode–Laser–Based Atomic Absorption Monitor Using Frequency–Modulation Spectroscopy for Physical Vapor Deposition Process Control," *App. Phys. Lett.*, vol. 67, No. 10, Sep. 4, 1995, pp. 1375–1377.

Weizhi Wang, M. M. Fejer, R. H. Hammond, M. R. Beasley, and C. H. Ahn; M. L. Bortz and T. Day, "Atomic Absorption Monitor for Deposition Process Control of Aluminum at 394 nm Using Frequency–Doubled Diode Laser," *App. Phys. Lett.*, vol. 68, No. 5, Feb. 5, 1996, pp. 729–731.

R. Fischer, J. Klem, T. J. Drummond, R. E. Thorne, W. Kopp, H. Morkoc and A. Y. Cho, "Incorporation Rates of Gallium and Aluminum on GaAs During Molecular Beam Epitaxy at High Substrate Temperatures," *J. Appl. Phys.*, vol. 54, No. 5, pp. 2508–2510, May 1983.

F. G. Celii, Y.–C. Kao, A. J. Katz, and T. S. Moise, "Real–time Monitoring of Resonant–tunneling Diode Growth Using Spectroscopy Ellipsometry," *J. Vac. Sci. Technol. A*, vol. 13, No. 3, pp. 733–739, May/Jun. 1995.

Jan P.A. van der Wagt and J. S. Harris, Jr., Reflection High–energy Electron Diffraction Intensity Oscillations During Molecular–Beam Epitaxy on Rotating Substrates, *J. Vac. Sci. Technol. B*, vol. 12, No. 2, pp. 1236–1238, Mar./Apr. 1993.

Alan Fried, James R. Drummond, Bruce Henry and Jack Fox, "Versatile Integrated Turnable Diode Laser System for High Precision: Application for ambient measurements of OCS", *Applied Optics*, vol. 30, No. 15, May 20, 1991 (see entire document).

W. E. Ahearn, "Optical Bridge for an Atomic Absorption Rate Monitor and Control System", *IBM Technical Bulletin*, vol. 14, No. 1, Jun. 1971 (see entire document).

METHOD OF CONTROLLING MULTI-SPECIES EPITAXIAL DEPOSITION

CROSS-REFERENCE TO RELATED APPLICATIONS

This is a continuation-in-part of application Ser. No. 08/657,614, entitled "Integrated Multi-Channel Optical-Based Flux Monitor and Method", filed May 31, 1996, by P. Pinsukanjana et al., which application is incorporated by reference herein.

STATEMENT AS TO RIGHTS TO INVENTIONS MADE UNDER FEDERALLY SPONSORED RESEARCH AND DEVELOPMENT

This invention was made with Government support under Grant/Contract Nos. DMR-9120007, MDA 972-94-10002, DAAH 0493-G-1256, awarded by the National Science Foundation and the Army. The Government has certain rights in this invention.

BACKGROUND OF THE INVENTION

1. Field of the Invention

The present invention involves controlling the deposition attributes such as deposition rate and composition of an epitaxial layer being fabricated from a plurality of atomic species in a vacuum chamber.

Many widely known deposition techniques such as molecular beam epitaxy (MBE) and electron-beam evaporation are used in the fabrication of many types of devices including electronic and opto-electronic devices. An important need exists to improve both the accuracy and the yield of high performance electronic and opto-electronic device fabrication. Some examples of these devices are Resonant Tunneling Diodes (RTD), Vertical Cavity Surface Emitting Lasers (VCSEL), electro-optical modulators, and quantum well lasers. Often, the process for making these devices involves depositing thousands of distinct epitaxial layers while maintaining strict control of the composition and thickness of each layer. In addition, there are further constraints such as:

1) limited access of the monitoring system to the vacuum deposition chamber.

2) monitoring system has to be non-invasive to the deposition process.

3) error due to noise and drift has to be sufficiently small during the course of the deposition.

4) monitoring system must have a high rejection of stray light from the surrounding environment.

5) monitoring system must not be affected by special requirements such as sample rotation during MBE deposition.

6) the monitoring system should be portable and most of the setup should be remote from the deposition chamber.

Currently, many epitaxial deposition techniques such as electron-beam evaporation and Molecular Beam Epitaxy (MBE) lack good deposition monitoring systems which have the ability to monitor in real-time the deposition rate as well as composition during multi-component epitaxial deposition. Included among these monitoring systems is the technique of atomic absorption.

It has long been recognized that atomic absorption can be used as a tool for monitoring of material deposition processes. Atomic absorption techniques generally involve passing a light beam through the molecular beam of the MBE process and then measuring the resulting intensity of the light beam. The more atoms that are being deposited, the greater the atomic absorption of the light, resulting in a lower intensity of the light remaining. The light beam must have a wavelength that corresponds with the atomic species desired to be measured. In this way the deposition of the epitaxial layers with respect to a particular atomic species can be measured. Recently, because of a need for better non-invasive real-time feedback during the deposition process, increased attention has been turned toward monitoring techniques using atomic absorption of the molecular beam flux.

2. Description of the Related Art

There have been many prior monitoring systems which utilize the atomic absorption technique. However, the prior art discloses the monitoring of just one channel at a time with the possibility of combining several independent one-channel units to build a multi-channel system. These multi-channel systems do not integrate the channels and therefore require additional port space in the vacuum chamber.

Appl. Phys. Lett. 60 (5) Feb. 3, 1992, p. 657, (Klausmeier et al.), discloses the passing of a modulated light beam through the molecular beam of an MBE process and then passing the light beam through a bandpass filter and into a photomultiplier tube. The filter passes only a particular emission line so that only the deposition of the atomic beam flux corresponding to that particular wavelength is measured. If more than one atomic beam flux is being deposited on the substrate then the Klausmeier device can only measure the deposition rate and composition of one atomic species.

J. Vac. Sci. Technol. B 12(2), Mar/Apr 1994, p. 217, and J. Vac. Sci. Technol. A 13(3), May/Jun 1995, p. 1797, disclose a system similar to Klausmeier's and the implementation of multiple channels is not directly addressed.

Appl. Phys. Lett. 63 (23), Dec. 6, 1993, p. 3131, and Appl. Phys. Lett. 65 (1), 4 July 1994, p. 4, disclose a dual-beam configuration with two channels but it is not optimized for the limited optical access that exists in most MBE and electron beam evaporation systems. The two channels are not integrated to follow one path through the molecular beam and therefore require additional port space in the vacuum chamber.

SUMMARY OF INVENTION

It is an object of the present invention to present a novel method of controlling an epitaxial deposition of a flux of material onto a substrate. The method comprises depositing a flux of material having a plurality of atomic species onto the substrate, monitoring the deposition of the plurality of atomic species using atomic absorption of light, and modifying the deposition in response to the measured atomic absorption.

It is a further object of the invention to provide an apparatus for controlling the deposition of a plurality of atomic species onto a substrate comprising means for depositing a plurality of atomic species onto the substrate, means for monitoring the deposition attributes of the film by the use of atomic absorption and means for modifying the deposition means.

It is a further object of the invention to provide a device having epitaxial layers manufactured according to the steps of placing a substrate in a vacuum chamber, forming an epitaxial layer on the substrate from the flux of material, transmitting a plurality of light beams through the flux of material, measuring the atomic absorption of the light beams by the flux of material, and modifying the flux of material in accordance with the measured atomic absorption so that a desired rate of formation of the epitaxial layers is achieved.

The present invention is optimized for low absorption level and integrated multi-channel atomic absorption monitoring using fiber optics. The invention includes an integrated multi-channel optical monitoring system which simultaneously monitors the atomic absorption of distinct atomic species during epitaxial deposition. The concept of atomic absorption is that when light of a particular wavelength passes through an atomic species which absorbs light of the same wavelength then some of the light is absorbed by the atomic species. Therefore, one light source is needed for each atomic species desired to be measured. In a preferred embodiment, the light source corresponding to each atomic species is atomic emission radiation from a hollow cathode lamp. There are at least two embodiments of the present invention. In both embodiments, the beams from the different wavelengths overlap inside of the vacuum chamber and are discriminated by different chopping frequencies. Under limited optical access, therefore, it is still possible to probe the atomic absorption of several atomic species simultaneously. In both embodiments, only one pair of through optical ports or one optical port with a set of mirrors is used in the vacuum chamber.

In a first embodiment, the light from each of the light sources is modulated at a distinct frequency by a mechanical chopper and then combined into one beam through a combining optical fiber bundle. The combined beam is divided into a reference arm and a signal arm and then collected by two optical fibers. The reference arm is used to compensate for lamp intensity drift. The light in the signal arm is sent through the region within the vacuum chamber through which the flux of material being deposited is passing. The signals are detected with two detectors. The modulated signals are recovered using lock-in amplifiers. This configuration is useful when optical access to the region is limited.

In a second embodiment, the light of each channel is initially kept separated and individually divided into the reference and the signal arms. The light in the reference arms and signal arms of all channels are chopped at different chopping frequencies. The light in the signal arm is sent through the region and then collected by another set of optical fibers. For each channel, the light in the signal arm and the light in the reference arm is then combined and detected with the same detector.

An advantage of the second embodiment is that the light from the signal and the reference arms for each atomic line are monitored by the same detector. Drift of these light beams with respect to each other due to the detector is virtually eliminated.

It is a further object of the invention to provide a data storage device that can be accessed by an application program being executed on a data processing system and that contains a certification data structure containing certification data. The certification data includes one or more of the deposition attributes.

It is a further object of the present invention to provide a method and apparatus for measuring the deposition attributes of a film already in existence by evaporating the atomic species in the film and monitoring the emitted atomic species using the integrated multi-channel atomic absorption monitor.

BRIEF DESCRIPTION OF THE DRAWINGS

Referring now to the drawings in which like reference numbers represent corresponding parts throughout:

FIG. 11 is a graph showing the atomic absorption signals as a function of deposition rate for Ga and In;

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Figure 1:
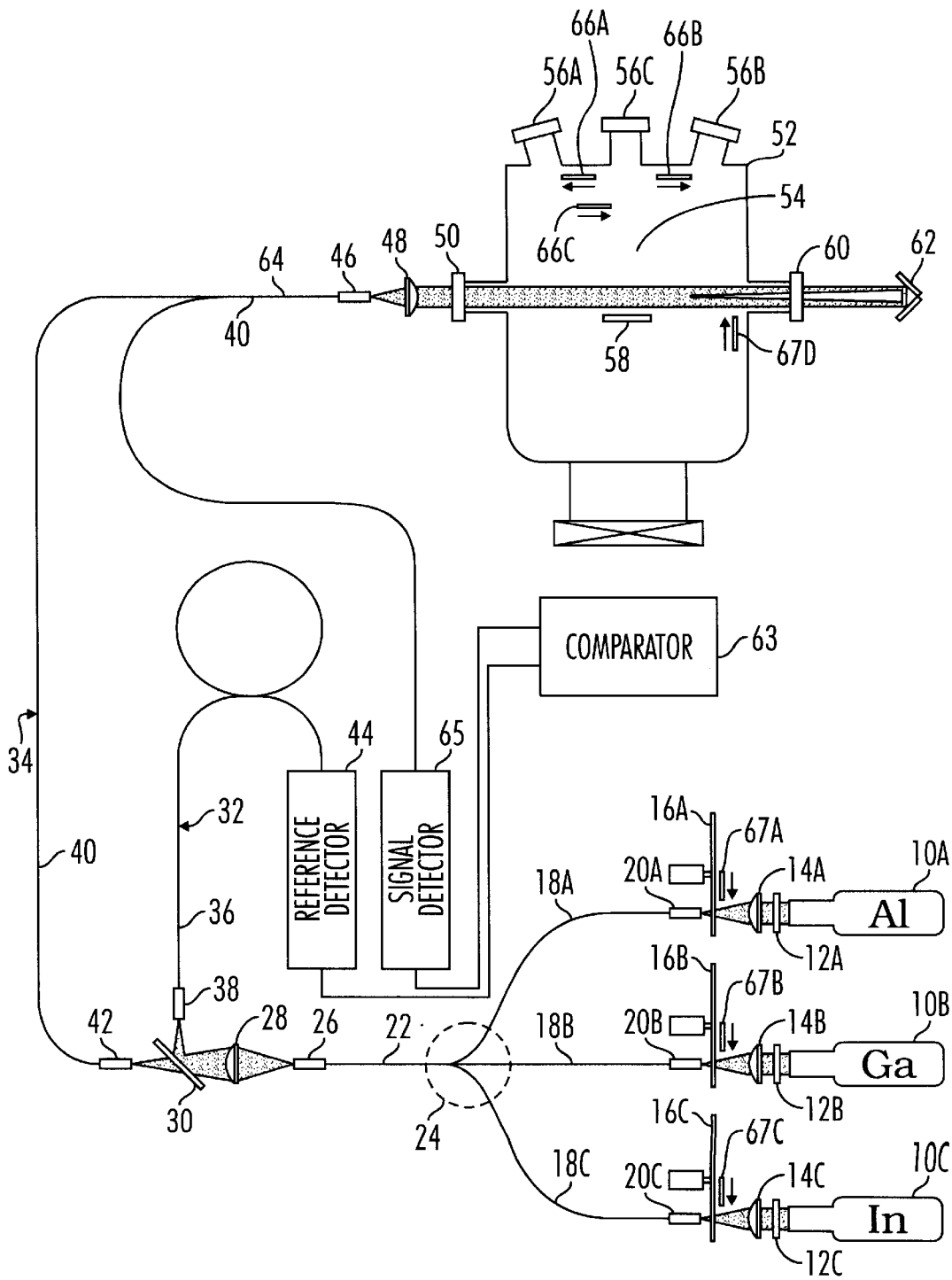
FIG. 1 is a schematic diagram of the first embodiment of the invention.
Figure 4:
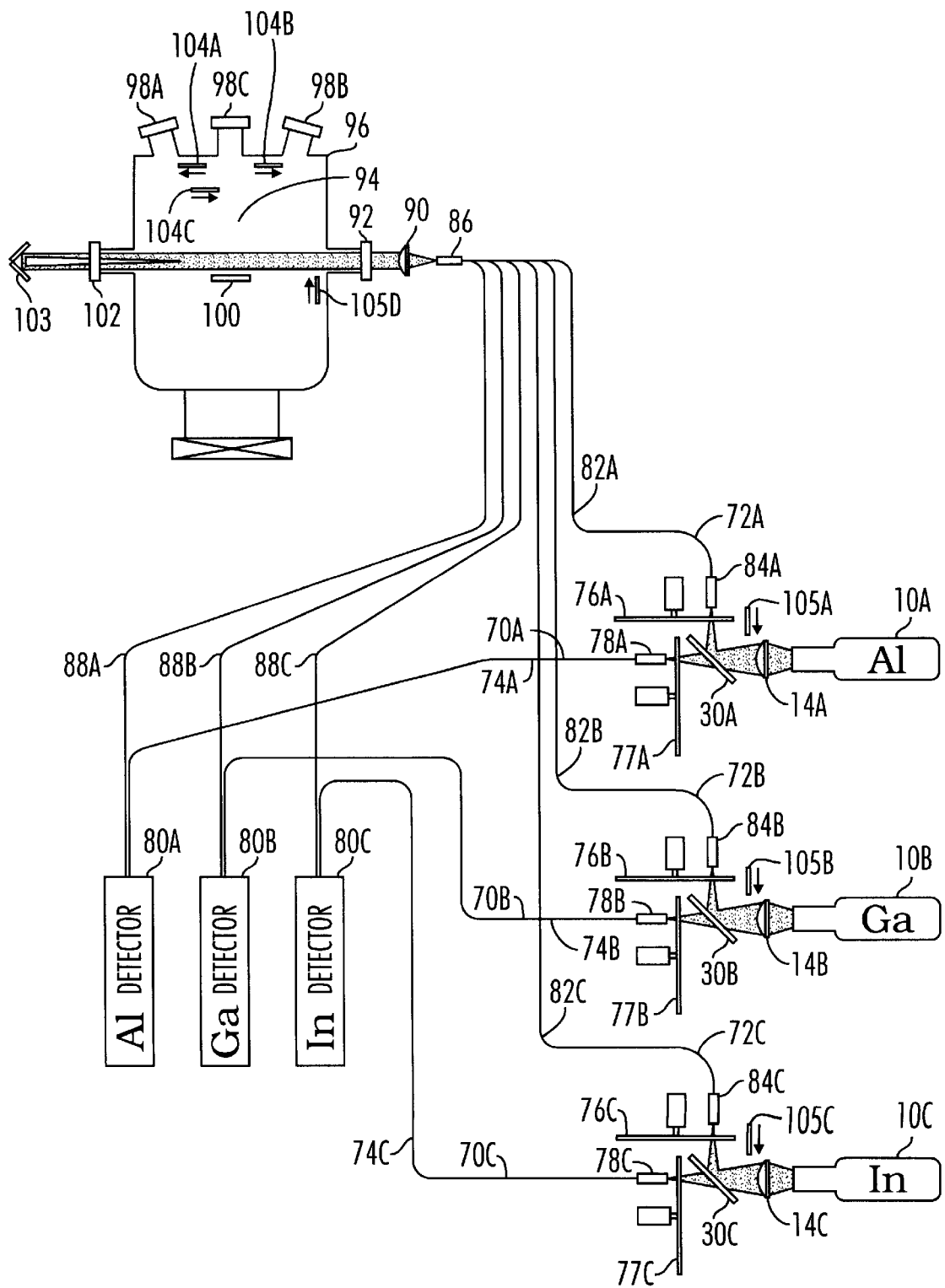
FIG. 4 is a schematic diagram of the second embodiment of the invention.

The schematic diagrams for two versions of the invention are shown in FIGS. 1 and 4, respectively. These FIGS. are specific to a three-channel optical based flux monitor (OFM) which monitor Al, Ga, and In simultaneously. The same principle may also be applied to a monitoring system with more or fewer channels and with other elements. Because each deposition system is unique, different optimization criteria have to be considered for each specific application. The description below is optimized for a solid source GEN II MBE system configured for III–V semiconductor material system, i.e., AlGaInAs. The typical deposition rates are in the range of $10^{-1}$ to $10^0$ monolayers per second. The devices are deposited under arsenic over-pressure and with unity sticking coefficient for the group III elements. However, one skilled in the art would recognize how to correct for non-unity sticking coefficient.

In the first embodiment, as shown in FIG. 1, the light sources 10*a*–*c* are hollow cathode lamps (HCL). Alternatively, the light sources 10*a*–*c* can be laser diodes or laser systems. Light source 10*a* is an Aluminum (Al) source and therefore it emits light with frequencies corresponding to Aluminum. Light sources 10*b* and 10*c* are Gallium (Ga) and Indium (In) sources, respectively. The HCL's can be operated under constant current or under constant light output mode. The light from the light sources 10*a*–*c* is filtered by narrow bandpass filters 12*a*–*c*, respectively, resulting in a bandpass output corresponding to each light source. Typically, for Al, Ga, and In, the narrow bandpass region is centered at corresponding emission lines which are at 395 nm, 417 nm, and 410 nm respectively with a typical bandwidth of 10 nm. Each bandpass output travels through a lens 14*a*–*c* respectively, which focuses the light. Each bandpass output is modulated by a mechanical chopper 16*a*–*c* such that each chopper has a frequency different than the other two choppers. By modulating the light, the system is less sensitive to the negative effects of stray light and the different channels can be demultiplexed. The bandpass outputs then enter optic fibers 18*a*–*c* respectively, through fiber input ends 20*a*–*c*, respectively. As can be seen by FIG. 1 each of the three bandpass outputs enter into a separate optic fiber designated as 18*a*–*c*, respectively. The three bandpass outputs are then combined into a combined beam in one optic fiber 22 using a trifurcating optical fiber bundle 24. A trifurcating optical fiber bundle has three optic fibers as inputs and one optic fiber as an output. The three bandpass outputs in the optic fibers 18*a*–*c* are combined into one combined beam in one optic fiber 22. The combining means does not have to be a trifurcating optical fiber bundle. If, for example, only two light sources are used then the combining means would combine the two bandpass outputs into one combined beam. The combined beam exits the optic fiber 22 through fiber output end 26 and then the combined beam goes through lens 28. The combined beam is then split by a beam splitter 30 into two arms. One arm is the reference arm 32; the other, the signal arm 34. The light split into the reference arm 32 is collected by optic fiber 36, with fiber input end 38. The light split into the signal arm 34 is collected by optic fiber 40, with fiber input end 42. The optic fibers 36 and 40 are multi-mode and have a 1 mm core diameter with numerical aperture (NA)=0.16.

The reference arm 32 (which is what makes this a dual beam system) is used to compensate for drifts in light source intensity. The three bandpass outputs in the combined beam of the reference arm 32 are detected by the detector 44. In the preferred embodiment the detector 44 comprises a collimating lens, filter, photomultiplier tube (PMT) and three phase sensitive lock-in amplifiers. The PMT measures the intensity of the bandpass outputs. The phase sensitive lock-in amplifiers are used to demultiplex the modulated bandpass outputs measured by the PMT. The detector 44 produces a plurality of reference signals, each reference signal corresponding to the intensity of a demultiplexed bandpass output. In the preferred embodiment as described here, the plurality of reference signals would be three reference signals corresponding to the three bandpass outputs. If, for example, four atomic species were to be detected, then four light sources and four phase sensitive lock-in amplifiers would be used.

The combined beam in the signal arm 34 travels in optic fiber 40 and exits the optic fiber 40 through fiber output end 46. The combined beam in the signal arm then travels through collimating lens 48 and through the first port 50 of vacuum chamber 52. The combined beam of the signal arm 34 is then sent through the vacuum chamber 52, passing through a region 54 between the sources 56 *a*–*c* and the substrate 58. The combined beam of the signal arm 34 then exits the vacuum chamber 52 through a second port 60 and is retroreflected by retroreflector 62 back into the vacuum chamber 52 via the second port 60. The optical ports on the MBE system of a preferred embodiment are 5 degree glancing-angle optical ports, 1.5" in diameter and approximately 3 feet apart. The retroreflector 62 comprises two mirrors situated such that the light reflected by the retroreflector 62 is returned along substantially the same path, but in the opposite direction, as the incoming light. The light from the signal arm 34 does not strike the substrate 58. The combined beam of the signal arm 34 then exits the vacuum chamber 52 through the first port 50. The combined beam of the signal arm 34, therefore, passes through the region 54 two times. It is within the scope of the present invention to have only a single pass through the region 54, in which case the atomic absorption would be reduced. The double pass through the region 54 increases the absorption level. If the vacuum chamber had more optical access, i.e., larger optical ports or shorter optical travel distance, multi-pass of the light in the signal arm through the region 54 could be implemented. This would increase the absorption level and might make monitoring of a much weaker absorption signal possible.

Because the returning beam—after bouncing through the two mirrors of the retroreflector 62—nearly retraces the optical path of the incident beam, it is refocused to a spot approximately the same spot size as the core diameter of the optic fiber 34. To increase light collection efficiency, the returning spot is focused onto a larger 1.5 mm core diameter collection optical fiber 64 with NA=0.39. The collection fiber 64 and the optic fiber 40 are within the same casing and therefore cannot be separately seen in FIG. 1. The collection fiber 64 then carries the combined light of the signal arm 34 to the detector 65. The detector 65 is the same as detector 44, except that the output of detector 65 is a probe signal and it is proportional to the intensity of the light received by the detector. While the remoteness of the monitoring system (detectors, etc.) made possible by the optic fibers is a desired characteristic, an alternative embodiment of the present invention could be implemented in which the detector 65 could be mounted on the port opposite the injection side (second port 60).

The reference signals and the probe signals are input to the comparator 63 that completes the comparison of the light in the signal arm 34 to the light in the reference arm 32 returning the atomic absorption level according to the normalization and calibration formulas described below. The comparator 63 is implemented in either hardware or software as is well known in the art.

The molecular beam shutters 66a–c and optical shutters 67a–d are used in conjunction with the normalization and calibration of the setup which is discussed below. The molecular beam shutters 66a–c block the flux of material from striking the substrate when closed. The optical shutters 67a–d block light from passing therethrough. The position of the shutters shown in the drawings is not meant to be limiting and one skilled in the art will realize that there are numerous locations in which these shutters can be placed and still block the light. The molecular beam shutters 66a–c and the optical shutters 67a–d can be made of any material that substantially blocks the passage of light. For example, a piece of cardboard can be used.

Figure 2:
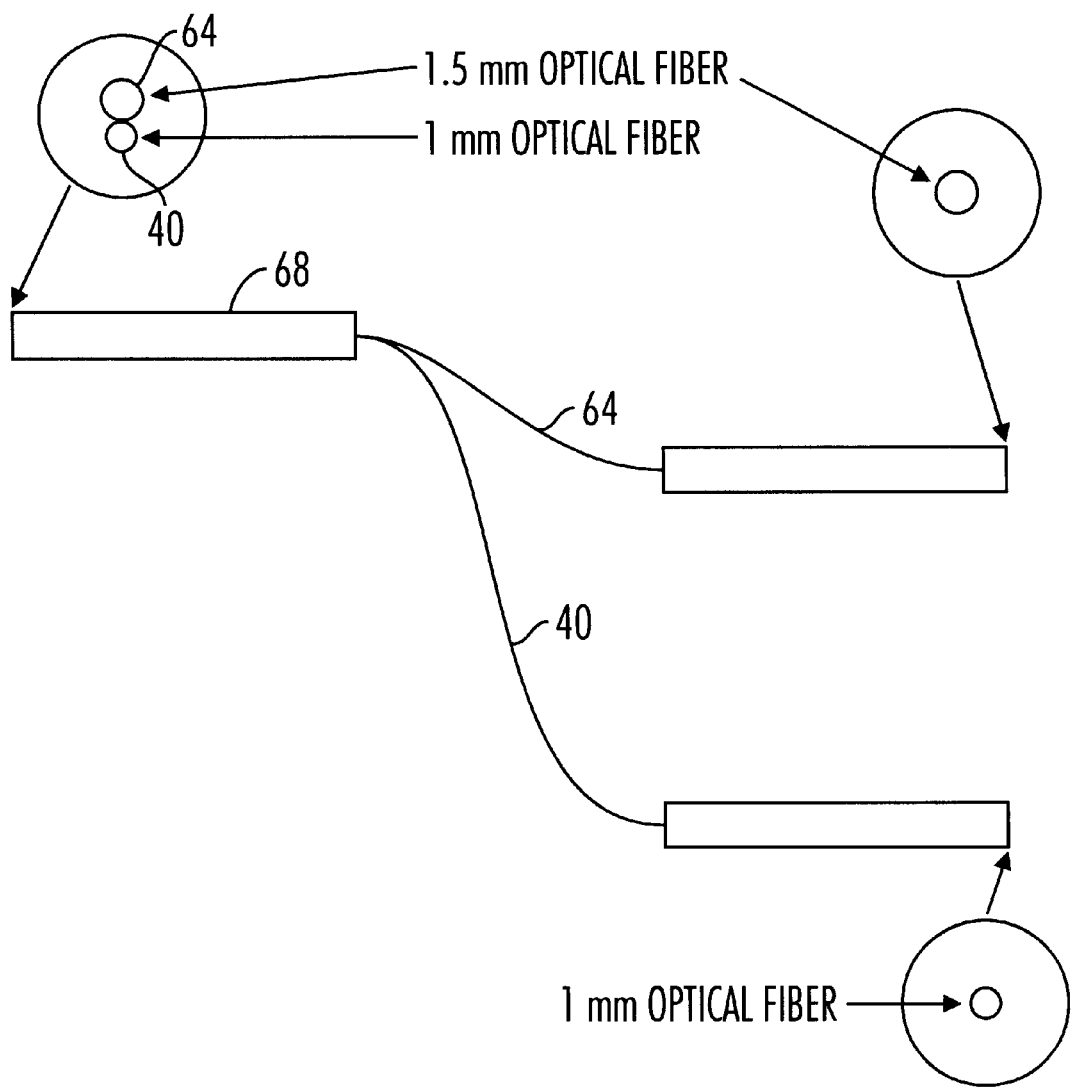
FIG. 2 is a view of the fiber optics in the first embodiment.

FIG. 2 is a view of the fiber optics in the first embodiment. The combined beam enters the vacuum chamber from optic fiber 40 (1 mm) and after making two passes through the region 54 is collected in collection fiber 64 (1.5 mm) to be delivered to the detector 65. As can be seen in both FIGS. 1 and 2, the optic fiber 40 and collection fiber 64 are adjacent to one another (in the same housing 68) near the injection and collection area which is near the fiber output end 46.

Figure 3:
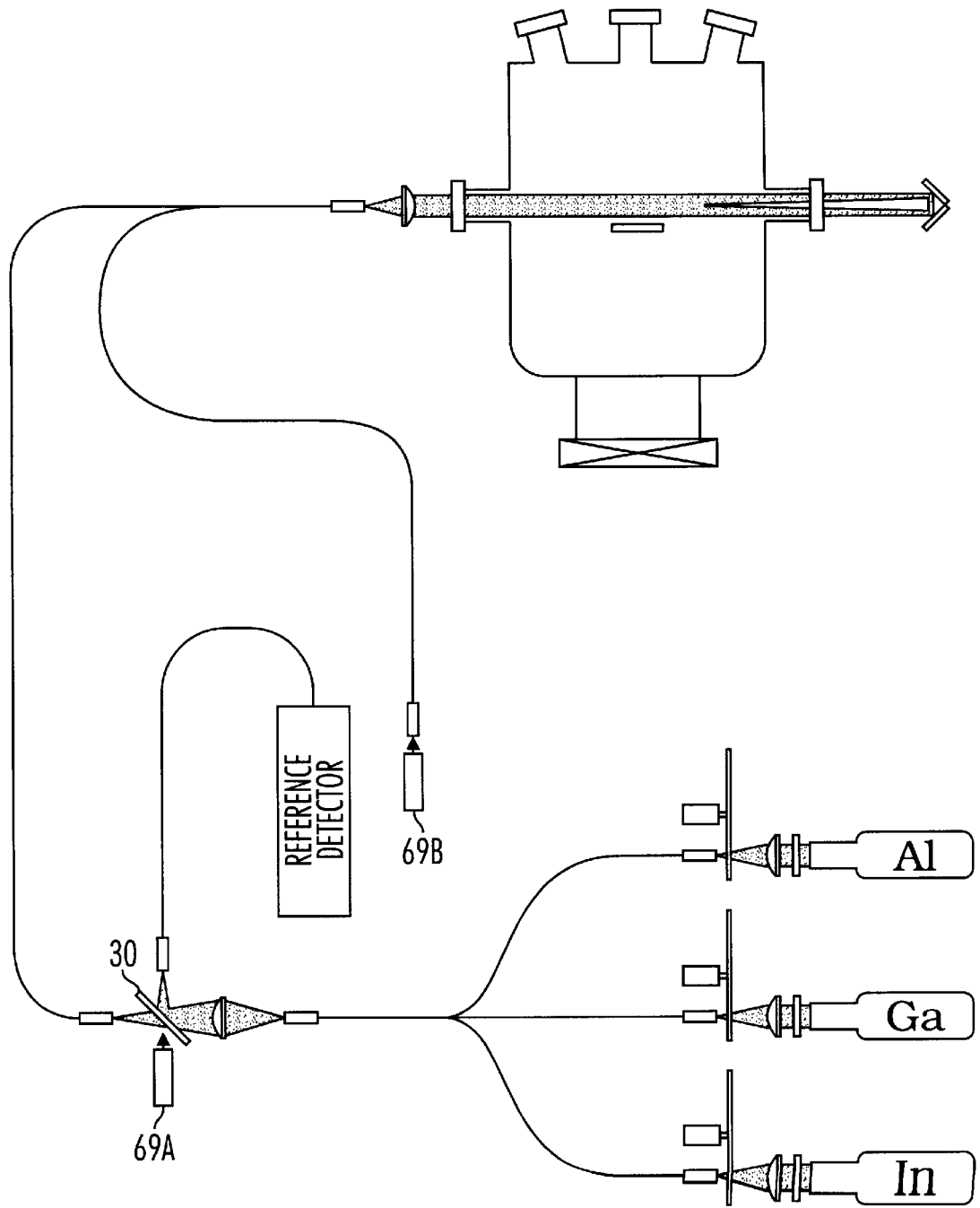
FIG. 3 is a schematic diagram of the first embodiment including the alignment light source.

FIG. 3 is a schematic diagram of the first embodiment including the alignment light source 69. The purpose of an alignment light source is to make alignment of the optical path through the vacuum chamber simpler by providing a brighter visual indication of the path of the light. The alignment light source 69 a is injected through one of the arms of the beam splitter 30 as shown in FIG. 3. The other alignment light source 69b replaces the detector 65 during alignment. Once properly aligned, the detector 65 can be re-connected back to the fiber optic network. Note that the optical alignment from a fiber end to a detector is generally not very critical.

In order to make the alignment of the optical path through the vacuum chamber 52 simpler, brighter light sources such as commercially available (red) diode lasers or high brightness blue LED's can be easily integrated into the optical setup without sacrificing system performance. Other possibilities for bright light sources are other types of lasers or lamps. Diode lasers and/or LED's are preferred because they are compact, economical, and easy to use.

Another advantage of diode lasers is that the optical beam is collimated. Additionally, diode lasers are brighter than LED's. However LED's have advantages too. Because the wavelength of a blue LED (450 nm) is much closer to the monitored wavelength of Al, Ga, and In (at 395, 417 and 410 nm respectively) than a red laser diode (670 nm), the optical beam profile of blue LED's through the fiber optic network will be more similar to those of the monitored wavelengths.

Based on experimental tests of the first embodiment, the long term drifts of the ratio signal—intensity of the light in the collection fiber 64 divided by the intensity of the light in the reference arm 32—is within 1 part in 1000 per hour over the course of a day.

FIG. 4 is a schematic diagram of the second embodiment of the invention. In the second embodiment the optical beam of each channel is kept separated from the optical beam of another channel until they are positionally and angularly multiplexed (integrated) to pass through the vacuum chamber together. The light sources are positionally and angularly multiplexed by placing the optic fibers 82a–c substantially adjacent to one another. The light sources 10a–c which can be hollow cathode lamps, laser diodes, laser systems or any other type of source of light, emit light which travels through lenses 14a–c and is then split by beam splitters 30a–c into reference arms 70a–c and signal arms 72a–c. The light in each of the signal arms 72a–c and the reference arms 70a–c is modulated with mechanical choppers 76a–c and 77a–c, respectively. There are a total of six choppers, all chopping at different frequencies, one for each of the reference arms 70a–c and one for each of the signal arms 72a–c for each of the light sources 10a–c.

After the light in the reference arms 70a–c has been modulated, it enters optic fibers 74a–c via the fiber input ends 78a–c. The optic fibers 74a–c carry the light to the respective detectors 80a–c.

The light in the signal arms 72a–c enters the respective optic fibers 82a–c, via the fiber input ends 84a–c. The three optic fibers 82a–c are adjacent to one another near the fiber output end 86 so that the light emitted is positionally and angularly multiplexed. In other words, the three light beams that exit the optic fibers 82a–c have paths that are substantially parallel to each other and the light beams overlap due to the fact that the light beams originate from different yet adjacent positions. Additionally, there are three collection optic fibers 88a–c which are linearly adjacent to the three optic fibers 82a–c. The light in the signal arms 72a–c exits the optic fibers 82a–c via the fiber output end 86 and passes through a common collimating lens 90, through a first port 92, and through a region 94 in the vacuum chamber 96 which is between the sources 98a–c and the substrate 100. The flux of material being deposited onto the substrate 100 flows from the sources 98a–c, through the region 94 and onto the substrate 100. Therefore, the positionally and angularly multiplexed light from the signal arms 72a–c passes through the flux of material being deposited onto the substrate 100. The light from the signal arms 72a–c does not strike the substrate 100. The light from the signal arms 72a–c exits the vacuum chamber 96 at a second port 102 and is retroreflected by retroreflector 103, nearly retracing the original optical path through the region 94. The light exits the vacuum chamber 96 through the first port and through the lens 90 which refocuses the light into three separate locations. Because the light is positionally and angularly multiplexed the refocused light enters the collection fibers 88a–c such that the light that exited optic fibers 82a–c enters collection fibers 88a–c respectively.

The light in the collection fibers 88a–c is then received by the detectors 80a–c respectively. Because the light in the signal arms 72a–c is modulated at a different frequency than the light in the reference arms 70a–c, the detectors 80a–c are able to identify which light is from the signal arms 72a–c and which is from the reference arms 70a–c. Each of the detectors 80a–c produces a probe signal, which is proportional to the intensity of the light received from the respective signal arms 72a–c, and a reference signal, which is proportional to the intensity of the light received from the respective reference arms 70a–c. Each pair of probe and reference signals originating from the same light source (for example, one of the group of light sources 10a–c are compared to each other to determine the atomic absorption of the particular atomic species having the same wavelength as the corresponding light source. The comparison step can be done in the detectors 80a–c or in a separate comparator. The probe signal generated by detector 80a is compared to the reference signal generated by detector 80a to determine the atomic absorption of the Aluminum species. Likewise, the probe signal generated by detector 80b is compared to the reference signal generated by detector 80b to determine the atomic absorption of the Gallium species. Lastly, for example purposes only, the probe signal generated by the detector 80c is compared to the reference signal generated by detector 80c to determine the atomic absorption of the Indium species.

In an alternative embodiment there are a total of six detectors. One detector is connected to each of the optic fibers 88a–c in the signal arms 72a–c and one detector is connected to each optic fiber 74a–c in the reference arms 70a–c.

The second embodiment also must be normalized and calibrated. The molecular beam shutters 104a–c and optical shutters 105a–c are the same as the molecular beam shutters 66a–b and the optical shutters 67a–d respectively.

Figure 5:
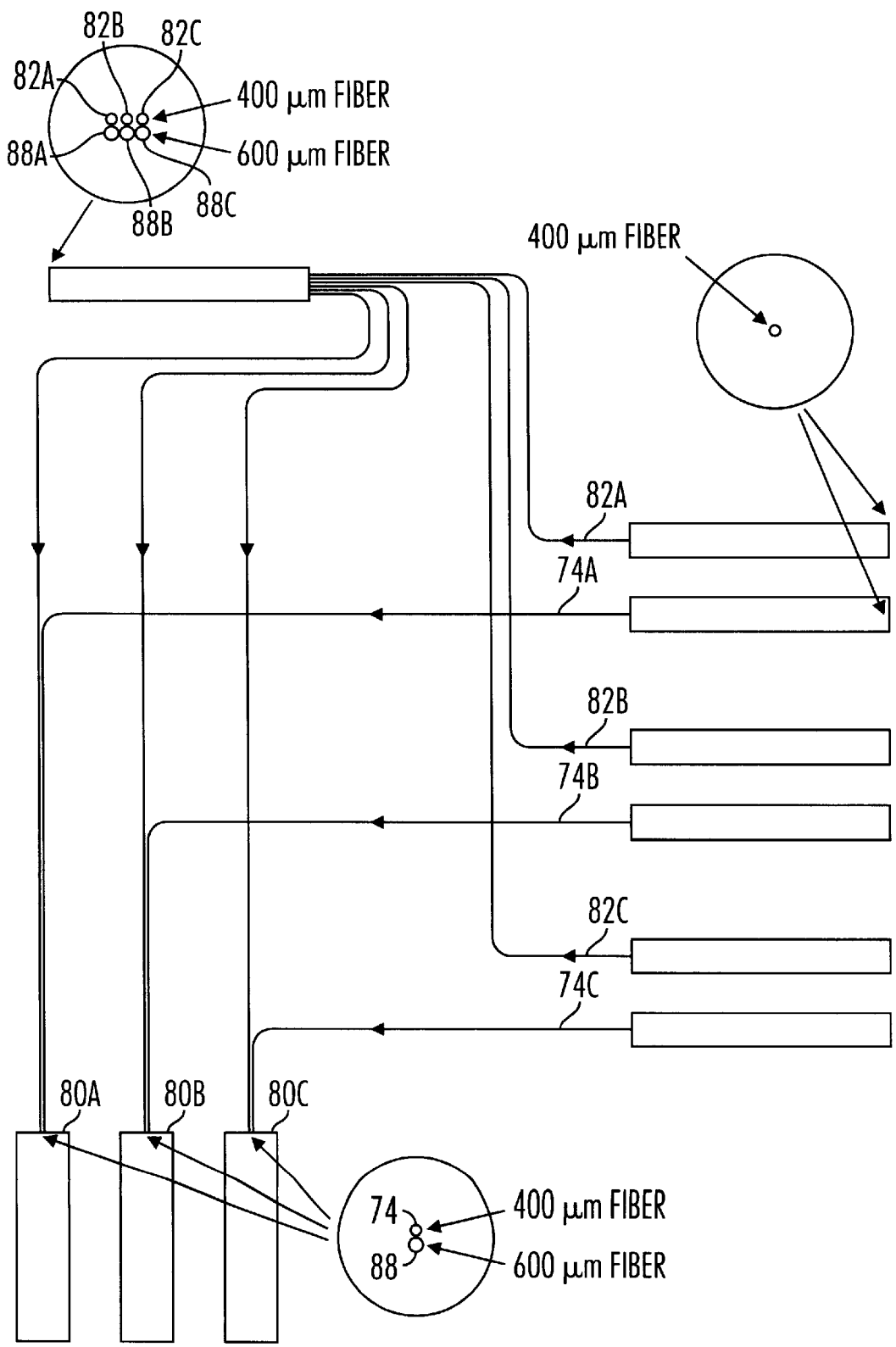
FIG. 5 is a view of the fiber optics in the second embodiment.

FIG. 5 is a view of the fiber optics in the second embodiment of the present invention. The optic fibers 82a–c leading to the vacuum chamber and the optic fibers 74a–c of the reference arms 70a–c (which lead to the detectors 80a–c) are shown in cross section to have a diameter of 400 micrometers, NA=0.16 and a cladding diameter of 0.2501", for example. The collection fibers 88a–c are also shown in cross section to have a diameter of 600 micrometers with NA=0.39. The collection fibers 88a–c lie adjacent and underneath optic fibers 82a–c, respectively, as shown in FIG. 5. These six optic fibers are encased in a cladding. In this arrangement of the optic fibers, the light from optic fiber 82 a makes a double pass through the region 94 and is then focused into the collection fiber 88a. The light from optic fiber 82b is collected in collection fiber 88b and the light from optic fiber 82c is collected in collection fiber 88c. As can be seen in the cross section of the optic fibers entering the detectors 80a–c, the optic fibers 74a–c are joined into one cladding with their corresponding collection fiber 88a–c which then enter the corresponding detector 80a–c.

Figure 6:
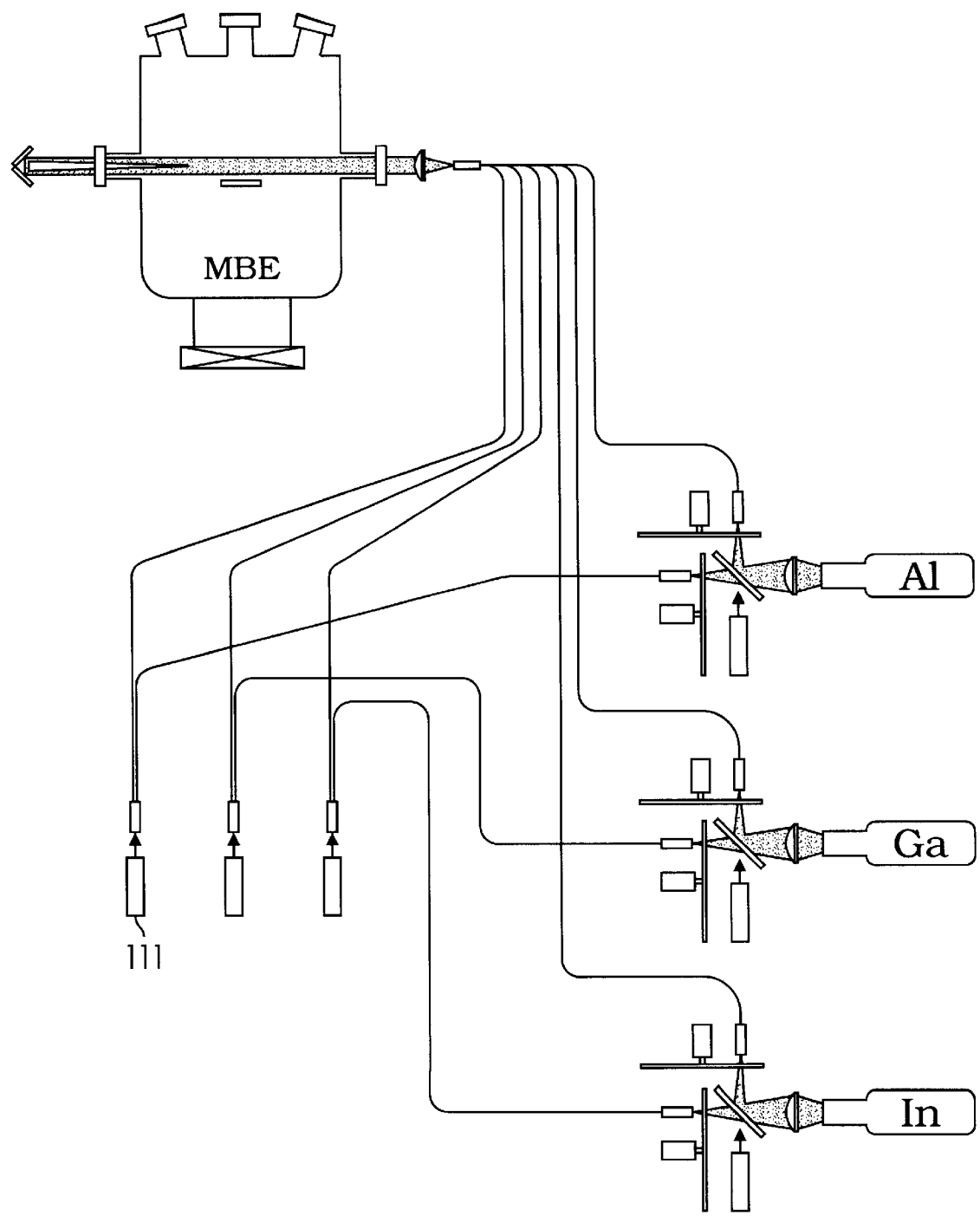
FIG. 6 is a schematic diagram of the second embodiment including the alignment light sources.

FIG. 6 shows the alignment setup for the second embodiment. The alignment of the second embodiment follows the same concepts as for the first embodiment as described above. Three alignment light sources 111 are injected at each of the beam splitters 30a–c, and each of the detectors 80a–c are replaced by an alignment light source. Once the optics are properly aligned, the detectors 80a–c are reconnected back to the fiber optic network.

Figure 7A:
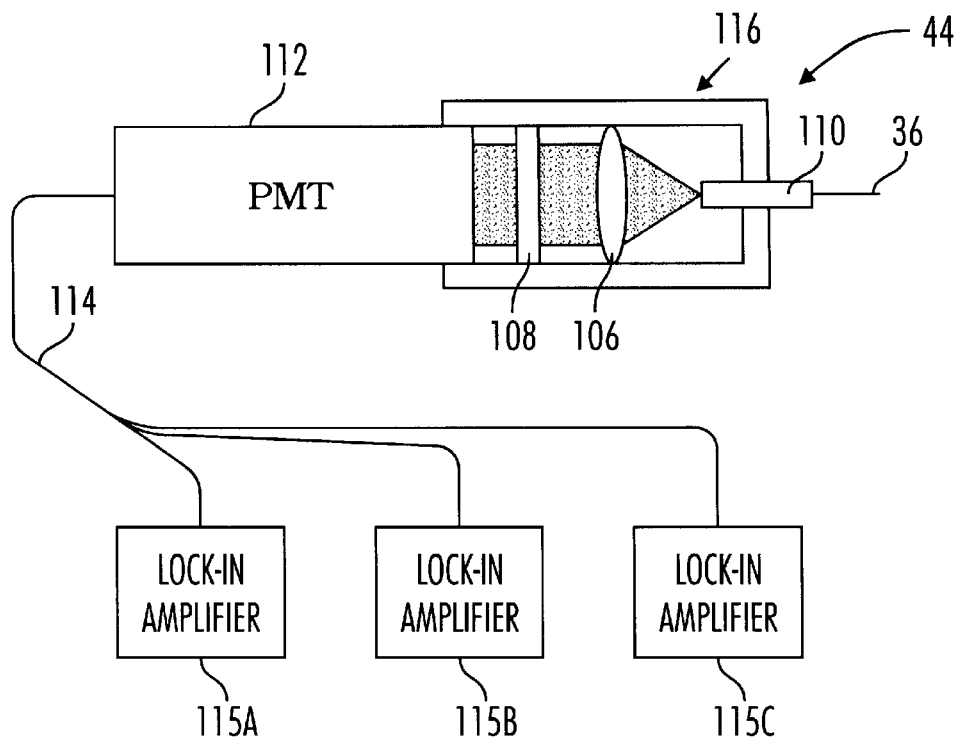
FIG. 7A shows a detector of the first embodiment of the present invention.

FIG. 7A shows the detector 44 used in the first embodiment of the present invention. This discussion also applies to the detector 65 which is identical to the detector 44. At the entrance of the detector 44, the light exits optic fiber 36 via optic fiber end 110 at the focal point of the lens 106. The light passes through the lens 106 and to a PMT 112. Directly in front of each PMT 112 is wide band-pass interference optical filter 108 used to filter out the unwanted radiation and to protect the PMT 112 from saturation. For the first embodiment of the present invention, 350 to 450 nm bandpass filters are used. The light strikes the PMT 112 and the signal corresponding to the intensity of the light striking the PMT 112 exits the PMT 112 through lead 114. The lead 114 carries the signal to the lock-in amplifiers 115a–c. There are three lock-in amplifiers in this illustration corresponding to the monitoring of three atomic species.

Figure 7B:
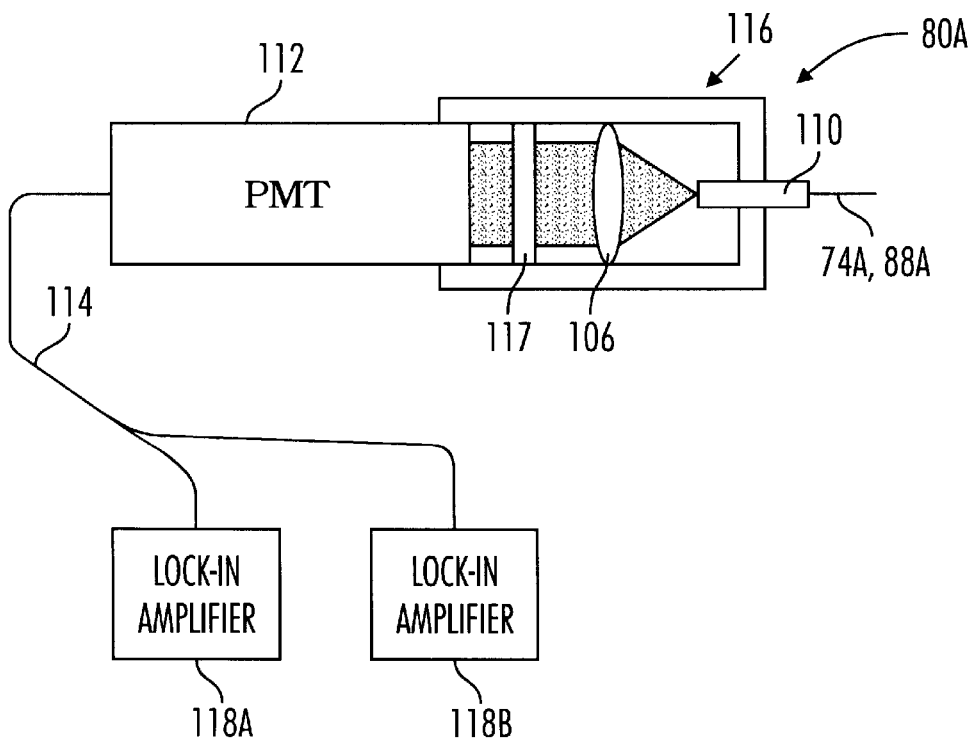
FIG. 7B shows a detector of the second embodiment of the present invention.

FIG. 7B illustrates a detector 80a for the second embodiment of the present invention. Note that the detector 80a could be any of the detectors 80a–c. The detector 80a is different from the detectors 44 and 65 of the first embodiment as shown in FIG. 7A because in the preferred embodiment detector 80 a has only two lock-in amplifiers 118a–b regardless of the number of atomic species being monitored.

At the entrance of the detector 80a, the optic fiber 74a and the collection fiber 88a are adjacent one another (to create spacial multiplexing) at the focal point of a collimating lens 106 (typically a biconvex lens), at which point such light exits the optic fibers via output fiber end 110. The lens 106 and PMT 112 are the same as in the first embodiment. The filter 117 is a narrow bandpass filter. The two lock-in amplifiers 118a–b are needed to demultiplex the reference signal and probe signal.

Based on experimental results, a typical RMS noise figure for the first embodiment is 1 part in 1500 of the transmitted signal when averaged over 1 sec of data. The accuracy improves with longer averaging time. Without port coating, signal drift of our current test system is no more than 1 part in 1000 over one hour. However, during operation with arsenic coating of the optical ports, the transmission signal drifts on the order of 1% per hour. By incorporating the use of heated optical ports and operating them above 200° C., signal drift due to arsenic coating can be eliminated.

Figure 8:
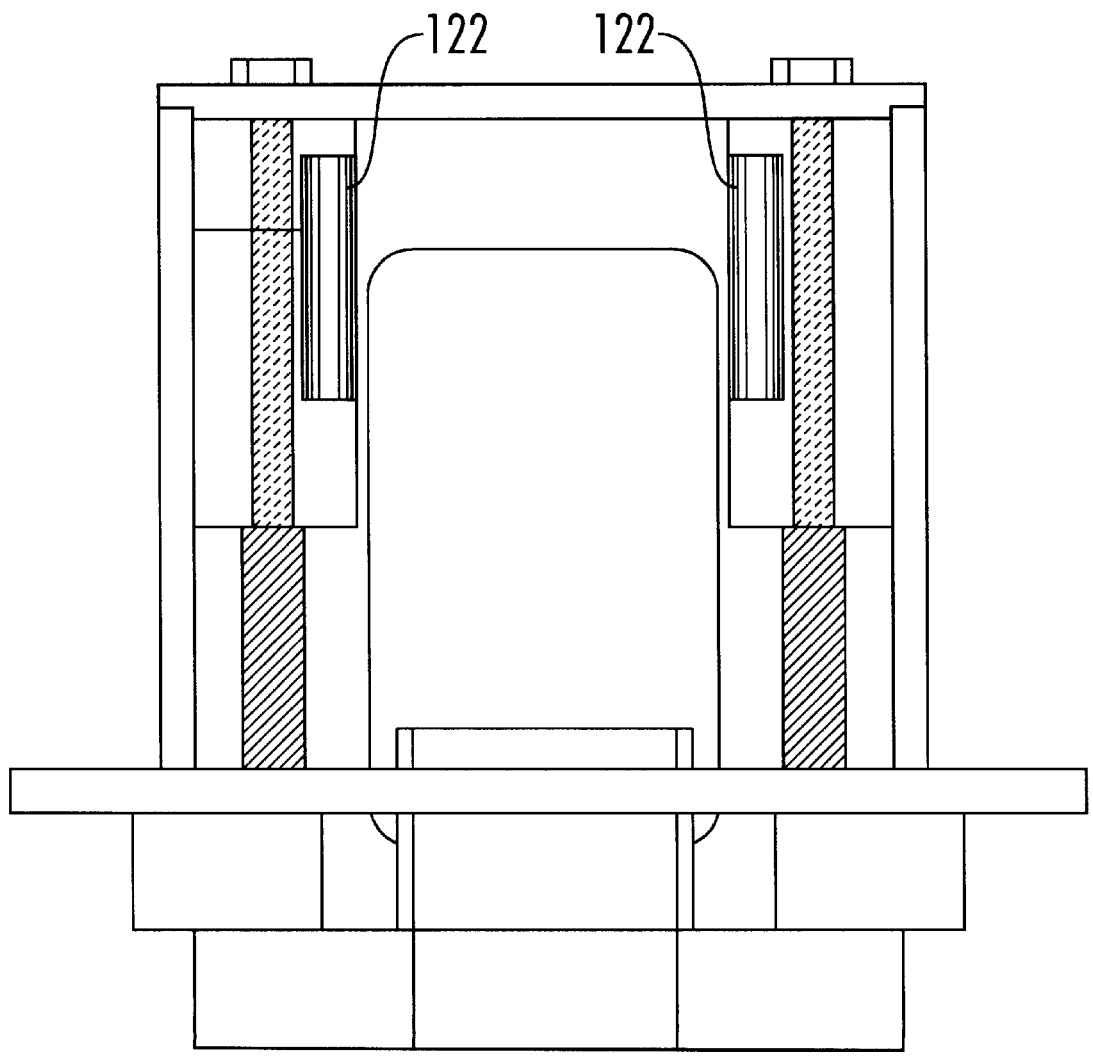
FIG. 8 shows a perspective view of the heated port of the present invention.

FIG. 8 shows a perspective view of the heated port of the present invention. For each port, a thermal couple 120, placed between the side of the port and the cylindrical heating element 122, along with a standard PID controller (not shown), is used for temperature regulation. The heated ports are continuously operated in the range of 300 to 450 degrees C. During several months of operation, arsenic coating of heated ports was virtually eliminated. The optic fiber 40 (in the first embodiment) or optic fibers 82a–c and collection fibers 88a–c (in the second embodiment), the collimating lens 106 and a pair of flat mirrors (the retroreflector 62 or 103) are all enclosed along with the heated ports within a light tight housing 116. An additional benefit of the heated port is that the above mentioned components that are within the port are all kept at a constant temperature throughout the day for improved stability.

Experiments with the first embodiment have been performed to compare the atomic absorption intensity of the molecular beam (in an MBE system) to the deposition rate measured by Reflection High Energy Electron Diffraction (RHEED) oscillations. The results are included here for a better understanding of the present invention.

Figure 9:
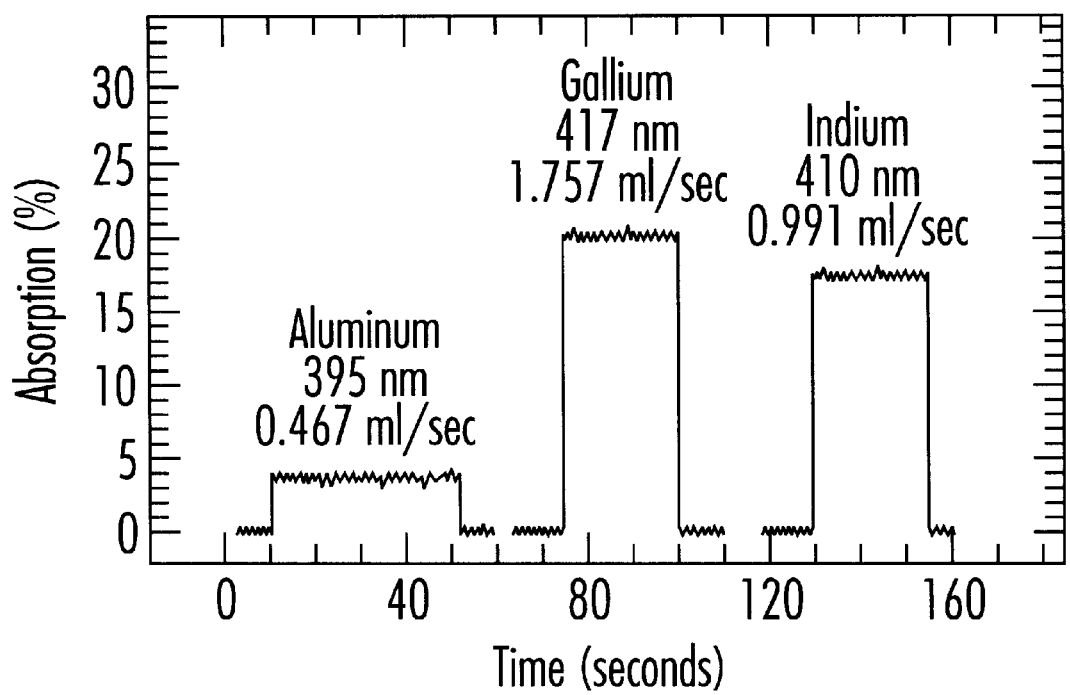
FIG. 9 is a graph of absorption signals for three different sources.

In the experimental arrangement, one pair of 5° glancing-angle optical ports on an MEE system was modified for use with the Optical-based Flux Monitor (OFM). The optical ports on the MBE system are 1.5" in diameter and approximately 3 ft. apart. Both ports have UHV mechanical shutters. The light in the signal arm passes through the vacuum chamber in front of the substrate and is then reflected back by a pair of flat mirrors (retroreflector 62). The returning light is collected by the collection fiber 64 (1.5 mm core diameter) which carries the light to the detector 65. FIG. 9 shows the absorption of Al, Ga, and In at the indicated deposition rates. The deposition rates were determined by observing RHEED oscillations. The monitored wavelengths are as indicated. Each trace corresponds to the source shutter operations of close/open/close. The absolute deposition rates were calibrated by RHEED oscillations. For data acquisition, a Macintosh Quadra 840 AV computer equipped with a multi-channel 16 bit Analog to Digital Converter board was used.

Because of offsets in the lock-in amplifiers and also due to stray light in the monitoring system it is preferred to normalize the measured signals. The effect of each light source intensity drift is normalized by dividing each probe signal by its corresponding reference signal. The reference signal is the signal measured in the reference arm when the light in the reference arm is not blocked (by the optical shutters 67a–c, for example) minus the signal measured in the reference arm when the light in the reference arm is blocked. For simplicity the discussion of normalization uses the reference numerals from the first embodiment. However, this is not meant to be limiting as these steps are also applicable to the second embodiment.

The comparison of the probe signal to the reference signal involves the following steps. First, the optical shutter 67d is closed and the intensity of the light in the signal arm is measured. This measured intensity will be referred to herein as the light blocked signal intensity. Next, the shutter 67d is opened and the shutter 66a or 66b, or both, whichever corresponds to the atomic species to be measured, is closed. The blocking of the molecular beam flux is typically achieved by valves or shutters. The measured intensity in the signal arm under these conditions is referred to herein as the flux blocked signal intensity. Lastly, the shutter 67d is opened and the shutter 66a or 66b, or both, whichever corresponds to the atomic species to be measured, is either partially or fully opened. The measured intensity in the signal arm under these conditions is referred to herein as the monitored signal intensity.

The light blocked signal intensity is divided by the reference signal resulting in the probe intensity offset, R. The flux blocked signal intensity is divided by the reference signal and the probe intensity offset, R, is subtracted off resulting in the flux blocked transmitted probe intensity, $T_0$. Lastly, the monitored signal intensity is divided by the reference signal resulting in the monitored probe intensity signal, $R+T_0-A$, where A is the absorption intensity (i.e. the intensity of light that is subtracted from the beam due to absorption by the flux of material and any other absorption along the optical path.)

Once the probe intensity offset, flux blocked transmitted probe intensity and monitored probe intensity signal are determined, then the normalized absorption is calculated. The normalized absorption which is the useful parameter is denoted as $$\gamma = A/T_0. \tag{1}$$

The normalized absorption is most useful because of its relationship to the deposition rate of the epitaxial layers. Under the deposition condition that re-evaporation of the monitored atomic species is negligible, the deposition rate is a one-to-one monotonically increasing function of absorption. Fortunately, re-evaporation is not a problem for our deposition condition which includes sufficiently low substrate temperature with arsenic over-pressure and deposition rate limited by the incident flux of the group III elements.

Since OFM measures the atomic absorption of the material in the region 54 being deposited and not the deposition rates directly, the OFM signals must be calibrated using other techniques. For MBE, RHEED is one way of calibrating the OFM. During calibration, the sample is not rotated. The calibrating RHEED electron beam is positioned at the center of the sample (substrate) where the monitored deposition rate should be independent of sample rotation. Typically, sample rotation is preferred during deposition because it improves epitaxial uniformity across the wafer. The disadvantage of rotation is that many monitoring techniques which directly probe the substrate such as RHEED, pyrometric interferometry, reflection and transmission spectroscopy, and ellipsometry become more difficult to implement. To partially circumvent this problem, many investigators have synchronized their data acquisition to sample rotation or averaged over several rotation periods. Therefore, the measurement speed for these other techniques is restricted by the period of sample rotation, while an OFM is free from this limitation.

Figure 10:
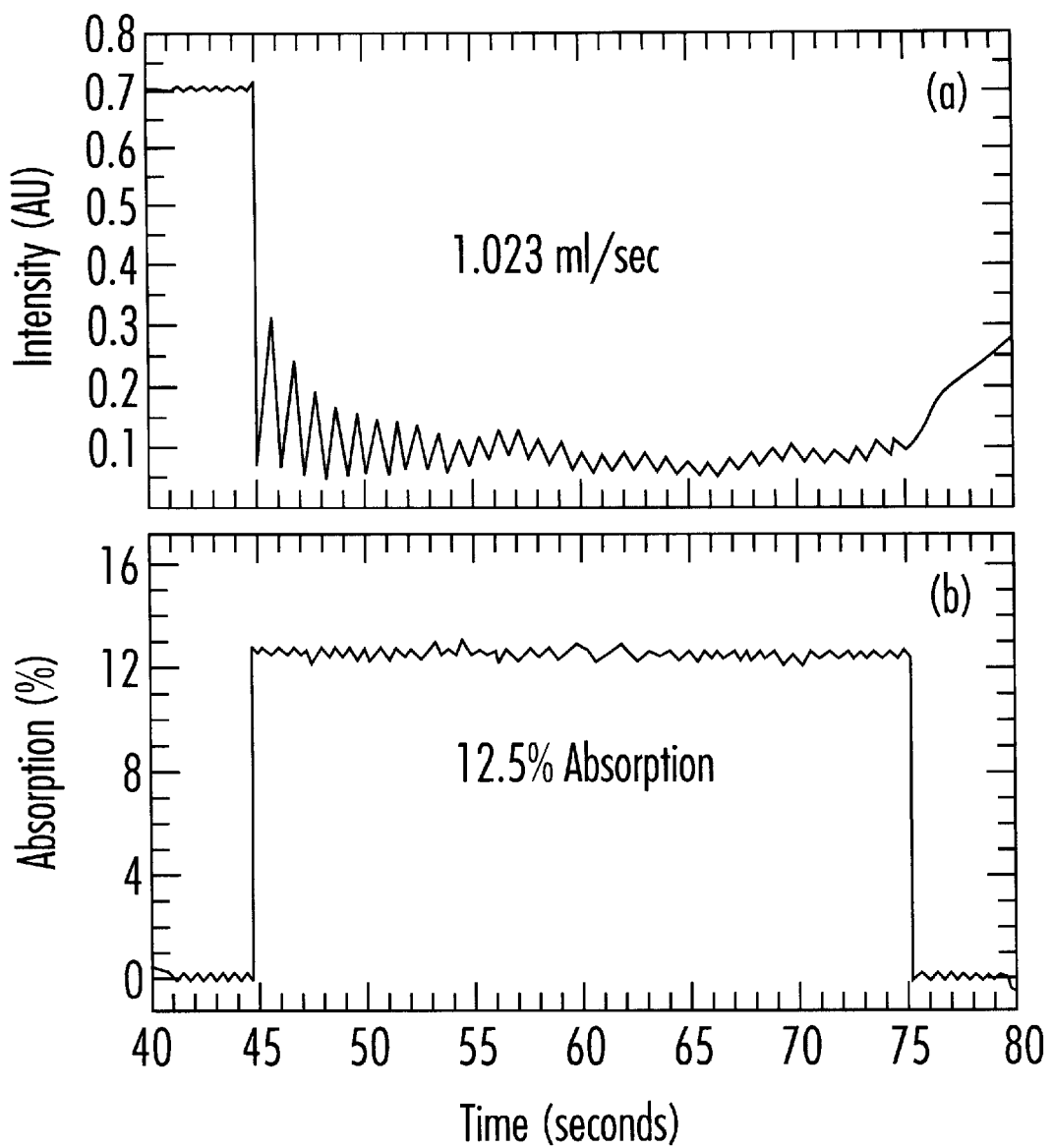
FIG. 10 is a graph showing the RHEED and the Ga absorption data for GaAs calibration.
Figure 11:
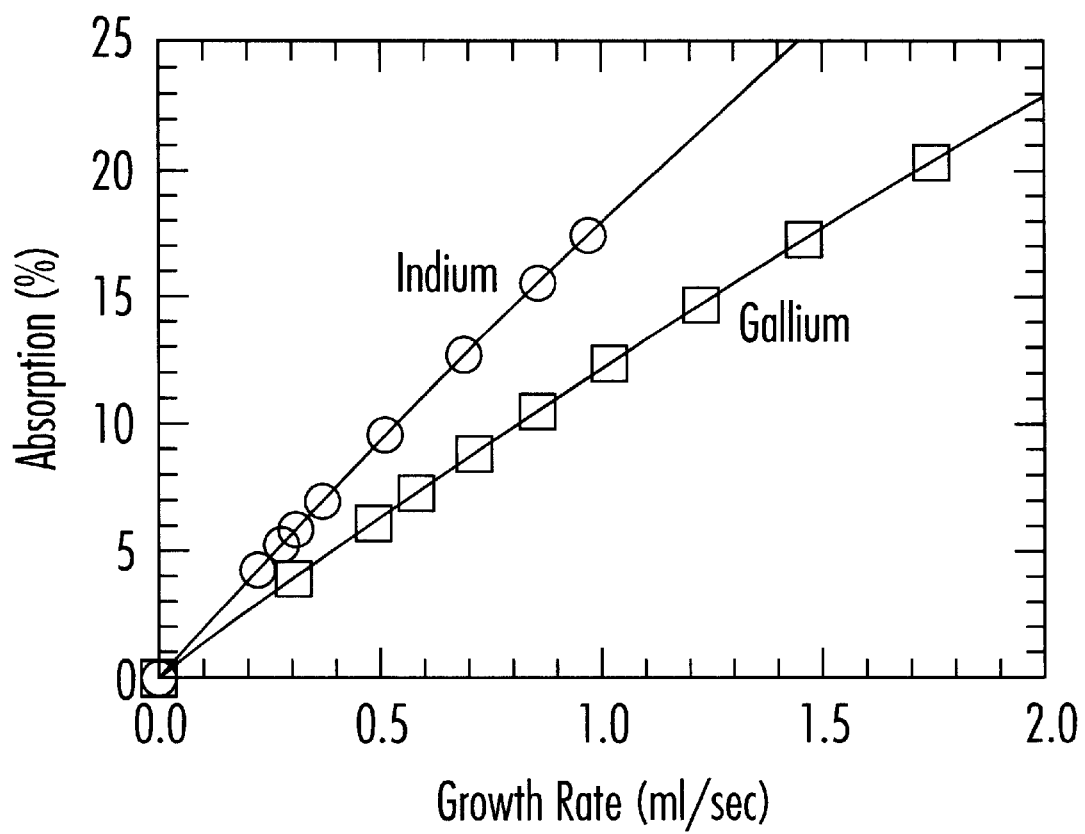

To calibrate the OFM, the atomic absorption of the material being deposited and RHEED oscillation signals are measured simultaneously. FIG. 10 shows the RHEED and the Ga absorption data for GaAs calibration. The deposition rate (1.023 monolayers/second) is determined from the period of RHEED oscillations. The absorption and RHEED data were taken simultaneously. Unlike the OFM signal, RHEED oscillations decay away over time; therefore, they become ineffective for monitoring deposition of thicker layers. In FIG. 11, atomic absorption signals as a function of deposition rate for Ga and In are shown. The substrate temperatures were 620 degrees C and 520 degrees C for the GaAs and InAs respectively. RHEED calibrations were measured on GaAs and InAs substrates, respectively. The lines through the data are the Modified Beer's Law fits of the form:

$$\gamma = 1 - \exp[-(\alpha + \beta r(r)] \tag{2}$$

where r is the deposition rate, and a and $\beta$ are the two fit parameters for the deposition rate dependent absorption coefficient, $(\alpha + \beta r)$. The deposition rate dependence of the absorption coefficient is likely due to a) the differences between the linewidth of atomic emission for an HCL and the absorption linewidth of the beam flux, and b) deposition rate dependent absorption coefficient not being a constant because the beam flux velocity changes with changing cell temperature. The discrepancy between the fit and the data is about 0.5%. However, by assuming a constant absorption coefficient ($\beta = 0$) for the fit, the discrepancy between the fit and the data increases significantly to about 2.5%.

The system developed is a compact multi-channel optical-based flux monitoring system based on atomic absorption. RHEED oscillations were used to calibrate the OFM so the system can accurately monitor in real-time the individual deposition rates of Al, Ga, and In.

Calibrating the OFM

Variations in the optical path cause constantly changing transmission problems. For example, during epitaxial deposition of compound semiconductors such as (AlGaIn)(AsPSb), there is typically an excess of the group V molecular beam fluxes (As and P). This excess flux of material will tend to coat the optical view ports thus changing their optical properties. To a lesser extent, this is still a problem even with the use of heated view ports which are designed to reduce the unintentional coating. Because the view ports are heated continuously, in between deposition runs when their is no flux of material, the excess fluxes that previously coated the view port are removed. The variations in the beam fluxes result in changes to the optical properties of the view port, optical transmission being the most noticeable. Because an atomic absorption flux monitor depends on transmitting an optical probe beam through the growth chamber, the fluctuation in time of the optical transmission property through the view ports results in intensity fluctuation of the probe beam. This argument also applies to other material systems such as, for example, HgCdTe, (AlGaIn)N, SiGe, and ZnSe.

One solution to the problem of varying optical transmission properties of the view ports or other variations in the optical path is to continuously calibrate the transmission property of the optical path. This additional calibration method is performed by the use of a calibration light source at a spectral region close to the monitored atomic absorption wavelength, but non-absorbing by the flux of material. The optical transmission measured by a calibration light source is then used in a calibration algorithm to compensate for changes to the optical path. Some possible calibration light sources are:

1) One of the existing monitored atomic absorption channels that is not being use for a particular growth deposition may be used as the calibration light source. For example, during the growth of AlGaAs structure, Al and Ga molecular beam fluxes are monitored (at wavelengths of 395 and 417 nm respectively). However the indium HCL lamp is not used. Therefore, the indium HCL lamp emission at 410 nm could be used to monitor the optical path as a calibration light source. For the first embodiment, this can be easily implemented without any modification to the optical setup.

2) A modulated white light source such as a xenon or a halogen lamp in combination with an appropriate narrow band pass optical filter centered near the monitored atomic absorption wavelength may be used as the calibration light source. This light source should be modulated at a distinct frequency (for example by a mechanical chopper).

3) An LED or a laser may be used as the calibration light source. For the case of Al, Ga, and In atomic absorption monitoring (at 395, 417, and 410 nm respectively), blue LED at 450 nm is preferred because it is a bright and inexpensive light source near the monitored wavelengths. The distinct periodic modulation can be accomplished electronically or by a mechanical chopper. For an LED or a laser diode, electronic modulation is preferred.

Figure 12:
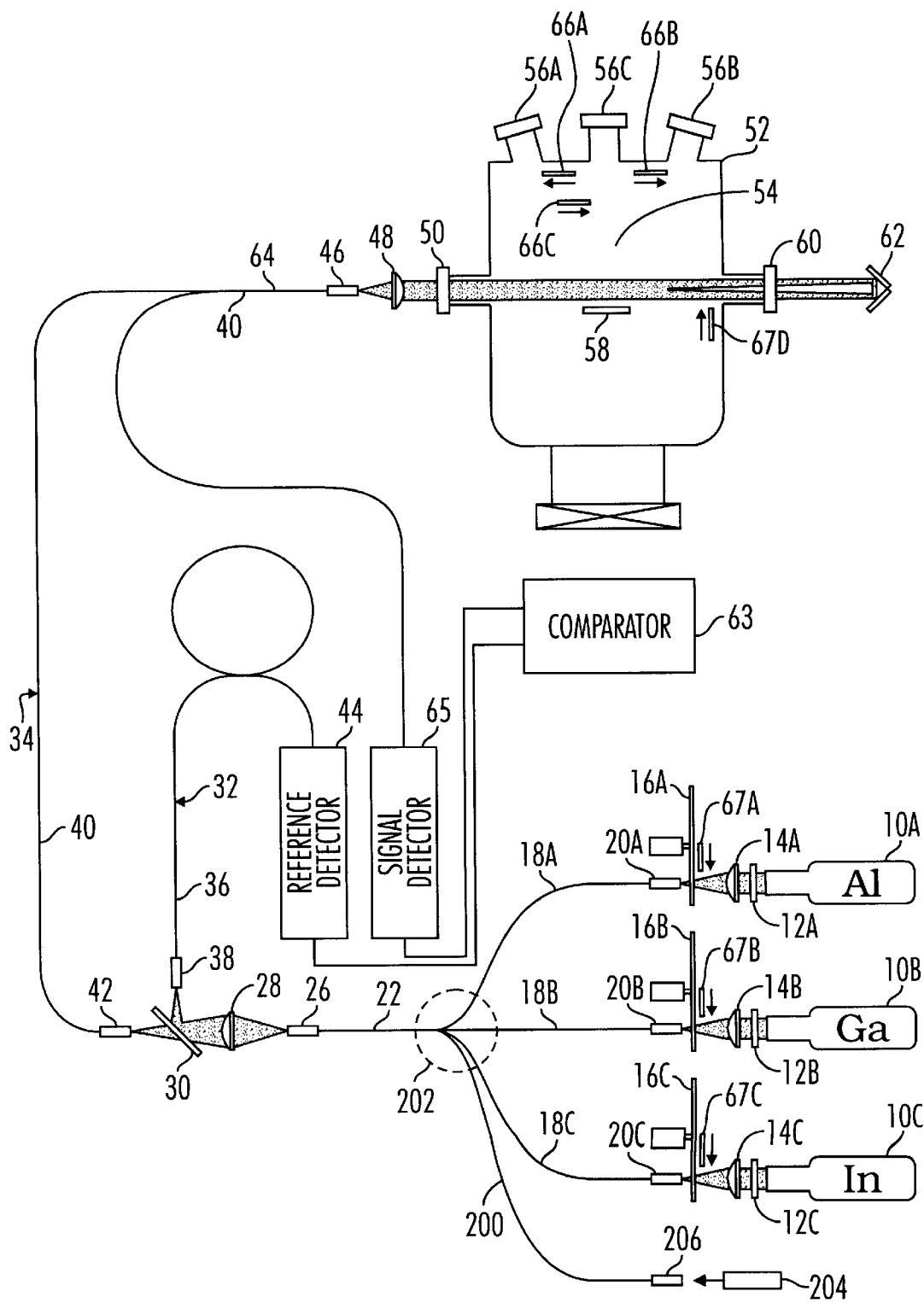
FIG. 12 is a schematic diagram of the first embodiment of the invention including a calibration light source.

There are several ways in which the calibration light source may be introduced into the optical system. FIG. 12 shows one possible setup for the first embodiment of this invention. An additional optic fiber 200 is incorporated into a four-way optic fiber bundle 202. A calibration LED 204 is attached to the fiber input end 206 of the optic fiber 200. For the specific case of monitoring Al, Ga, and In simultaneously, a blue LED is added as the fourth arm for the reasons mentioned above. The light from the calibration LED 204 is then combined with the light from the other light sources 10a, 10b and 10c in the combined beam in the optic fiber 22.

An alternative placement (not shown) of the calibration light source is at the beam splitter 30. The light would enter into the OFM at the beam splitter 30 and part of the light would be split into the reference arm 32 and part into the signal arm 34.

Figure 13:
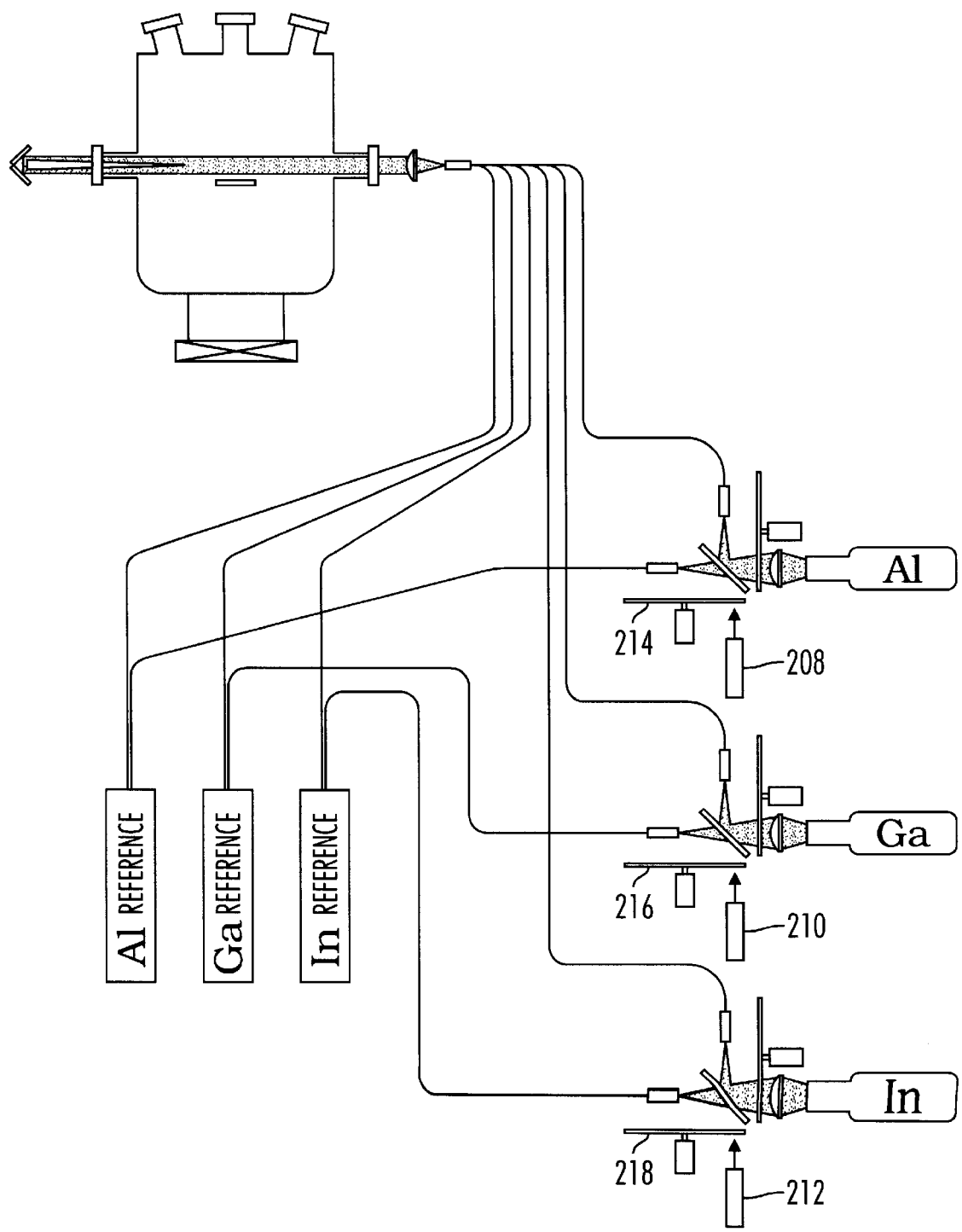
FIG. 13 is a schematic diagram of the second embodiment of the invention including three calibration light sources.

FIG. 13 shows the incorporation of calibration light sources into the second embodiment of the invention. The calibration LED's 208, 210, and 212 direct light through the mechanical choppers 214, 216, and 218, respectively. The chopped light passes into the beam splitters 30a, 30b, and 30c, respectively. One part of the light from the calibration LED enters the signal arm and the other part enters the reference arm.

The following measurements and computations are performed to normalize and calibrate the OFM. The discussion herein is directed to the embodiment shown in FIG. 12 but could be applied to other embodiments. First, the molecular beam shutters 66a–c are closed so that there is no flux of material. The light from the calibration LED 204 is channeled through the signal arm 34, including through the vacuum chamber and through the optical ports 50 and 60 and finally to the detector 65. The intensity of the light from the calibration LED, after it has traveled the length of this optical path, is then measured by the detector 65 and is referred to as the calibration flux blocked signal intensity. The calibration reference signal is the signal measured in the reference arm when the calibration light is not blocked (by the optical shutters 67a–d, for example) minus the signal measured in the reference arm when the calibration light in the reference arm is blocked by optical shutters 67a–c and by turning off the calibration LED 204. With respect to the calibration channel, $R_{cal}$ is defined as the light blocked signal intensity divided by the calibration reference signal. Then $T_{0,cal}$ is calculated using the following formula:

$$T_{0,cal} = [\text{calibration flux blocked signal/calibration reference signal}] - R_{cal} \quad (3)$$

After the above baselines have been determined, then the deposition runs (the runs to be monitored) are begun. During the deposition, the intensity measured by the detector 65 is referred to as the monitored signal intensity. It should be noted that there is a monitored signal intensity for each of the four channels. The monitored signal intensity for the calibration channel will be specifically referred to as the calibration monitored signal intensity. The value $T_{1,cal}$ is calculated using the following formula:

$$T_{1,cal} = [\text{calibration monitored signal intensity/calibration reference signal}] - R_{cal} \quad (4)$$

The calibrated normalized absorption, $\gamma_{cal}$, for a given channel is then calculated according to the following formula:

$$\gamma_{cal} = 1 - \frac{T_1/T_0}{T_{1,cal}/T_{0,cal}} \quad (5)$$

where $T_1$=[monitored signal intensity/reference signal]–R for the specific channel being monitored. Note that there are three $\gamma_{cal}$'s, i.e., one for each of the three channels, representing the calibrated normalized absorption for each of those channels. The reference signal used for computing $T_1$ and $T_0$ corresponds to the particular channel being monitored. In other words, when calculating $\gamma_{cal}$ for the aluminum channel the reference signal used to calculate $T_0$ and $T_1$ is related to the intensity of the light from the aluminum light source that is split into the reference arm.

It should be noted that when no calibration is necessary, i.e., $T_{1,cal}=T_{0,cal}$, then the above expression for $\gamma_{cal}$ becomes the same as the expression for $\gamma$ shown in equation (1) above. Therefore, calibration involves the addition of $T_{1,cal}$ and $T_{0,cal}$ to the formula for $\gamma$.

Real Time Control Using Atomic Absorption

Figure 14:
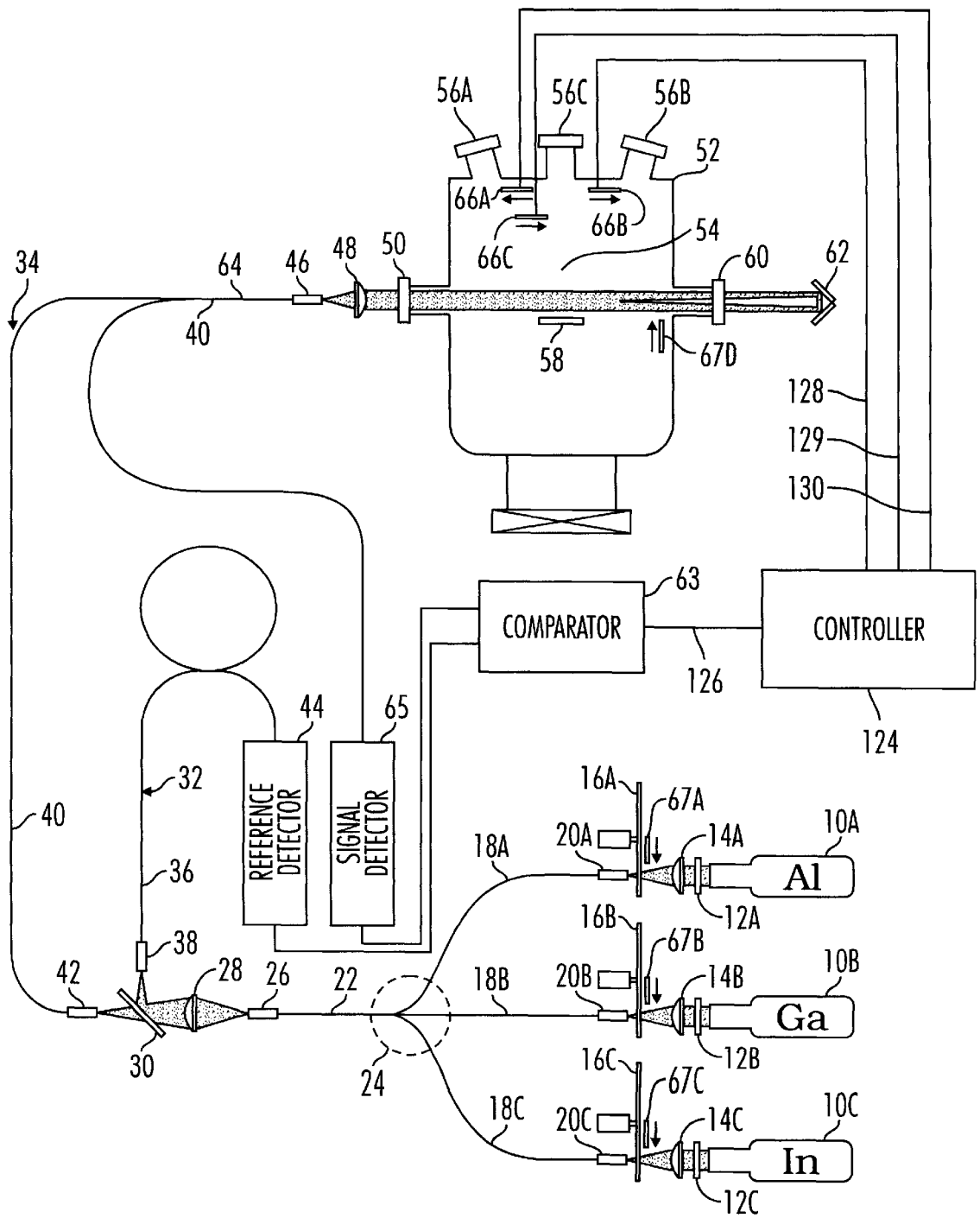
FIG. 14 is a schematic diagram of the first embodiment of the invention with a controller.

The present invention controls the deposition of atomic species onto a substrate in real time through the use of a controller. FIG. 14 illustrates the addition of a controller 124 to the first embodiment of the integrated multichannel optical based flux monitor, such that the present invention can control, in real time, the deposition process of more than one atomic species. The controller 124 is electrically connected to the comparator 63 through line 126. The controller 124 is also electrically connected to the molecular beam shutters 66a–c, via lines 128, 129 and 130, so that it can cause the shutters to open and close.

Figure 15:
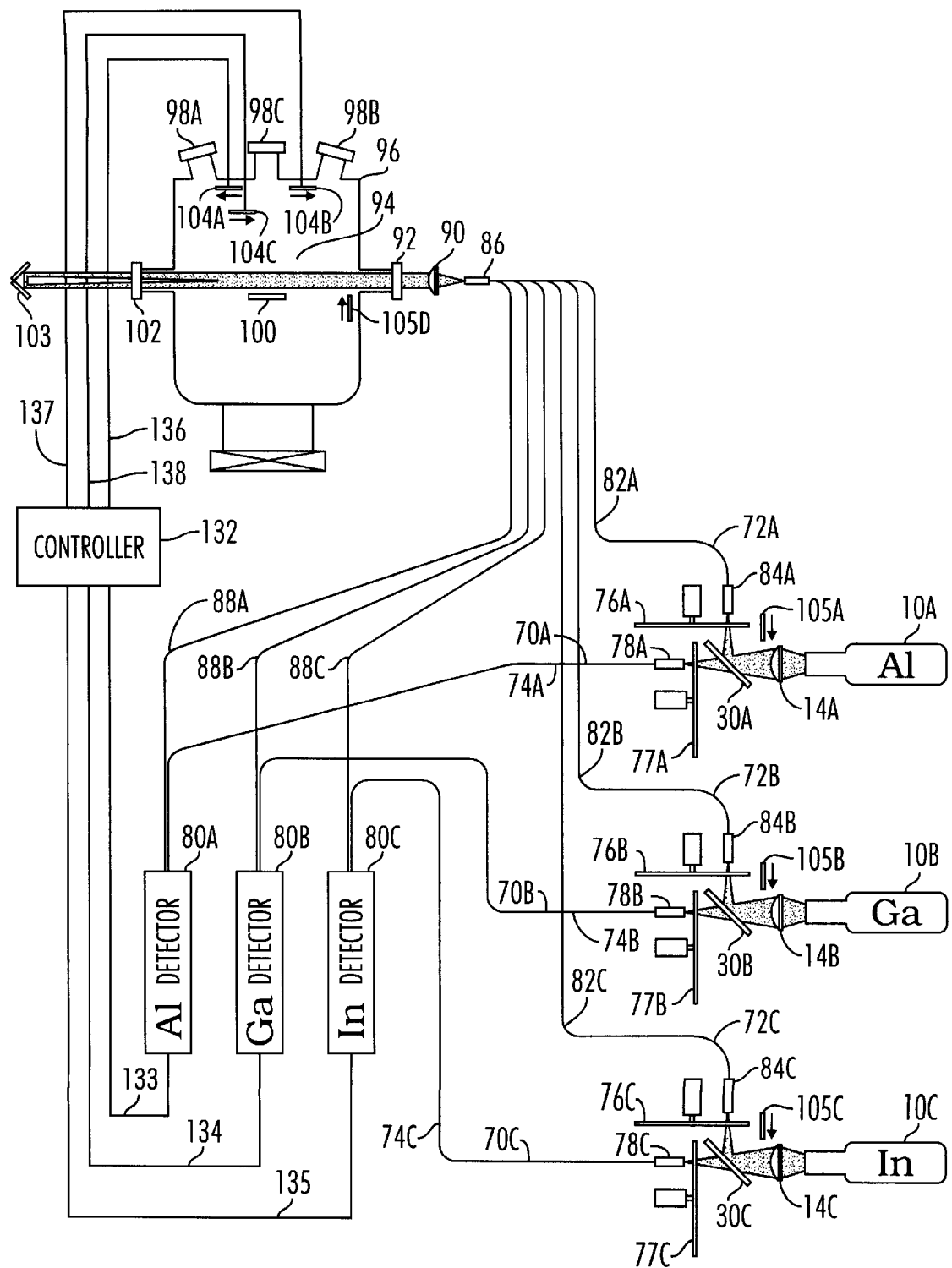
FIG. 15 is a schematic diagram of the second embodiment of the invention with a controller.

A similar control loop can be set up with the second embodiment. FIG. 15 illustrates the addition of controller 132 to the flux monitor of the second embodiment. Controller 132 is electrically connected to the Al detector 80a via line 133, the Ga detector 80b via line 134 and to the In detector 80c via line 135. The controller 132 is also electrically connected to the molecular beam shutter 104a via line 136, to the molecular beam shutter 104b via line 137 and to molecular beam shutter 104c via line 138. Therefore, the controller 132 can cause the molecular beam shutters 104a–c to open and close, thereby causing an increase or a decrease, respectively in the deposition of the atomic species from the respective sources 98a–c.

The steps involved in real time control of a deposition process are: depositing the flux of material on the substrate 58 in the vacuum chamber 52, monitoring the depositing step by measuring atomic absorption and modifying the depositing step, by changing the amount of material being deposited, in response to the measured atomic absorption.

In the following examples, the first embodiment of the monitor, as shown in FIG. 14, will be used. It should be noted, however, that the second embodiment, shown in FIG. 15, could also be used.

Controlling the deposition process to form a ternary quantum well with a specified photoluminescence (PL) energy is one exemplary application of the present invention. Various materials (atomic species) can be deposited on the substrate to create quantum wells, but a preferred quantum well is an $In_xGa_{1-x}As$ quantum well with GaAs cladding layers. Another example is an $Al_xGa_{1-x}As$ quantum well with AlAs cladding layers. Without loss of generality, the specific case of $In_xGa_{1-x}As$ quantum well will be discussed below. During a typical deposition process, there is constant arsenic over pressure and the deposition rates for these compound semiconductor layers are controlled by the deposition rate of the group III elements, namely Al, Ga, and In. Further, the growth conditions are typically chosen such that the group III elements have unity or at least near unity sticking coefficients.

Figure 16A:
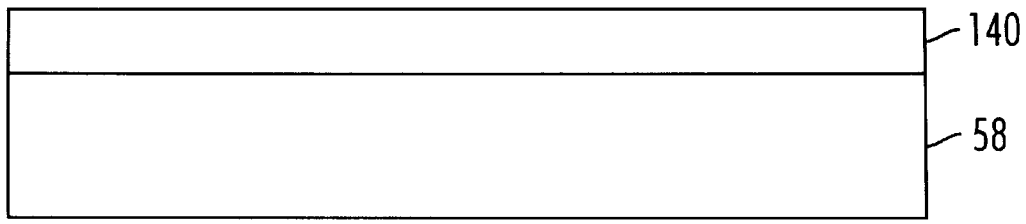
FIG. 16A shows a side view of the substrate and first cladding layer after the step of depositing the first cladding layer for a quantum well.
Figure 16B:
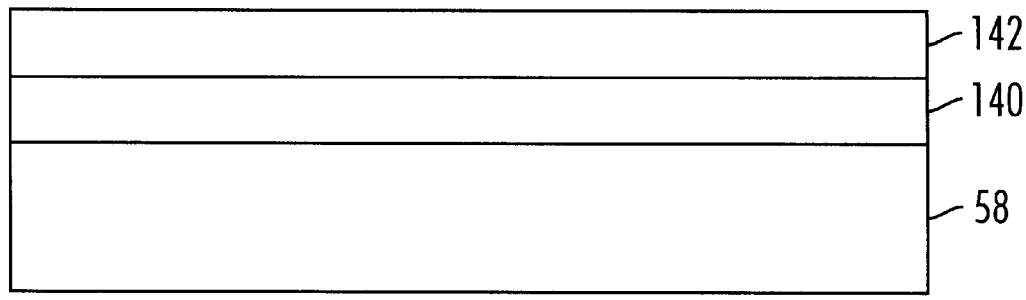
FIG. 16B shows a side view of the substrate, first cladding layer and quantum well after the step of depositing the quantum well.
Figure 16C:
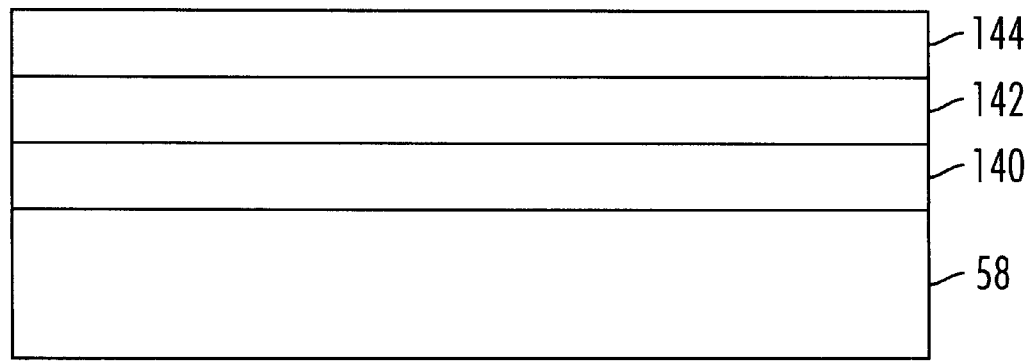
FIG. 16C shows a side view of the substrate, a first cladding layer, quantum well and a second cladding layer after the step of depositing the second cladding layer.

FIGS. 16A–C illustrate the layers of materials that are deposited to create a quantum well with cladding layers. The first step is to deposit a first cladding layer 140 on top of the substrate 58 as shown in FIG. 16A. In this example, the first cladding layer 140 is GaAs.

The next step, which is optional, is to pause deposition for 5 to 10 seconds for the interface between the GaAs and the substrate to smooth itself. This pause in the deposition is accomplished by closing the molecular beam shutters 66a and 66b or by turning the sources 56a–c off so they do not emit atomic species.

The next step is to deposit the InGaAs quantum well 142 as is shown in FIG. 16B. The quantum well 142 is deposited on top of the first cladding layer 138. All three atomic species In, Ga, and As are deposited simultaneously using the three sources 56a–c. The critical materials to be controlled are the Ga and In. The multichannel optical based flux monitor, described above, is used to monitor the atomic absorption of Ga and In to determine the instantaneous deposition rates of each using the techniques discussed above. The monitoring of the atomic absorption yields deposition attributes such as deposition rate and composition. The deposition attributes are then communicated to the controller 124 via line 126.

While the deposition is taking place, the controller 124 calculates the PL peak energy, $E(x,w)$, of the quantum well based on the deposition attributes. In the preferred embodiment, the PL peak energy of the quantum well is calculated using a model:

$$E(x, w) = A + B \cdot x + (C + D \cdot x) \exp\left(\frac{-w}{E + F \cdot x}\right) \quad (6)$$

where the coefficients A through F are determined numerically from prior depositions, x is the average mole fraction of the quantum well, and w is the well width. X and w are defined in terms of integrated thicknesses for In and Ga, $w_{In}$, and $w_{Ga}$, respectively. $w_{In}$ and $w_{Ga}$ are derived from the integrated atomic absorption signal based on equation (2). They are defined as follows:

$$w = w_{Ga} + k \cdot w_{In}, \text{ and } x = k \cdot w_{In}/w$$

where k is a coefficient which takes into account the difference in the lattice constant of the two species.

By correlating the measured PL peak energy to the measured deposition attributes in prior depositions the coefficients A through F are determined prior to the controlled deposition. Each prior deposition consists of depositing a quantum well, each under a different deposition condition (i.e., different composition and/or well width).

Both x and w are determined by atomic absorption during the real time control of the deposition process.

Next, the controller 124 compares the calculated PL peak energy, $E(x,w)$, to a predetermined energy set point, $E_{sp}$. The predetermined energy set point is the desired energy of the quantum well and it can, for example, be entered by the user prior to the deposition. As the deposition of the In, Ga and As continues, the PL peak energy of the quantum well so formed is reduced. If $E(x,w)$ is greater than $E_{sp}$, then the controller 124 allows the deposition to continue by keeping the molecular beam shutters 66a–c at least partially open. If $E(x,w)$ is less than $E_{sp}$, then the deposition of the Ga, In and Al atomic species is terminated by closing the molecular beam shutters 66a–c. A quantum well with peak PL energy very close to the desired energy set point can be achieved by such a control loop.

After the quantum well layer has been deposited, the InGaAs surface is allowed to smooth itself by pausing deposition for 5 to 10 seconds. This pause in the deposition is accomplished by closing the molecular beam shutters 66a–c or by turning the sources 56a–c off so they do not emit atomic species.

The last step is to deposit a second cladding layer 144 of GaAs (see FIG. 16C). The second cladding layer 144 is deposited on top of the quantum well layer 142 and provides a protective layer for the quantum well.

A second example of using the integrated multi-channel optical based flux monitor for control of the deposition process is controlling the deposition of a ternary digital alloy superlattice. In this example, the deposition of a digital alloy superlattice of $Al_xGa_{1-x}As$ with the average Al mole fraction x, will be discussed. Al is assumed to be the dominant specie.

Figure 17:
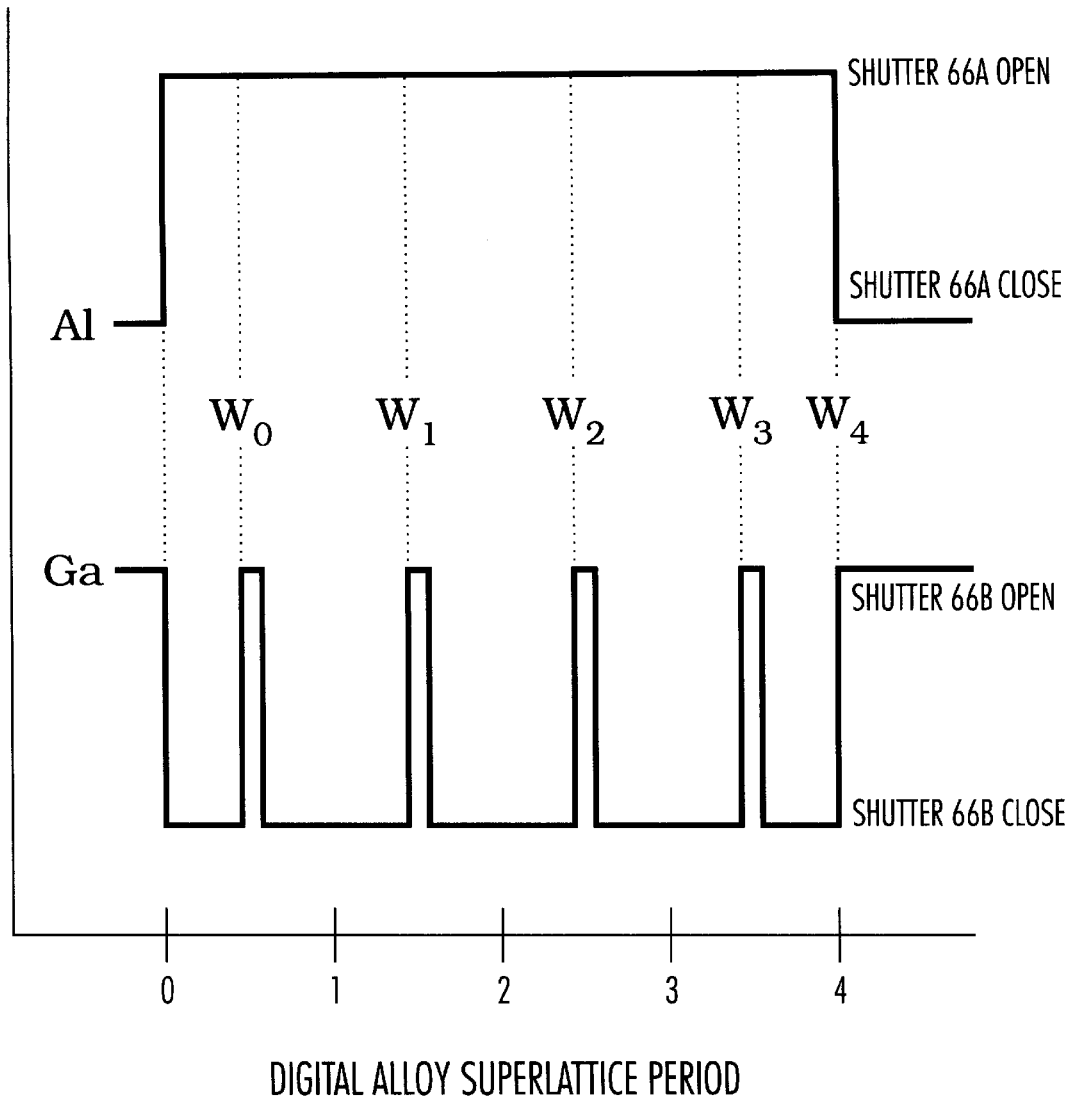
FIG. 17 is a graph showing the molecular beam shutter position as a function of the digital alloy superlattice period.

A layer of digital alloy superlattice is realized by depositing Al during the entire deposition process while periodically depositing short pulses of Ga in the center of each superlattice period. FIG. 17 shows the digital alloy superlattice periods along the x-axis and the opening and shutting of the molecular beam shutters 66a and 66b corresponding to Al and Ga respectively (for example), along the y-axis. The controller must open and close the molecular beam shutters 66a and 66b as shown in FIG. 17. The Arsenic molecular beam shutter 66c is constantly open allowing a constant Arsenic beam flux (i.e. the constant Arsenic over pressure).

A set of five input parameters required for defining a ternary digital alloy superlattice are:
  W total width of the superlattice,
  N number of periods of the superlattice
  x average Al mole fraction of the digital alloy superlattice,
  $r_{A1}$ most recent deposition rate of Al,
  $r_{Ga}$ most recent deposition rate of Ga.

W, N, and x are specified by the user. The most recent deposition rates may be supplied by the user or obtained from the last updated measurement of the deposition rates. Another equivalent set of five defining parameters are:
  $w_{AlI}$ thickness of Al during each period when the Ga pulse is off.
  $w_{Ga}$ thickness of Ga during each Ga pulse,
  $w_{Al2}$ thickness of Al during each Ga pulse,
  $t_1$ duration of Al deposition during each period when the Ga pulse is off,
  $t_2$ duration of each Ga pulse.

The relationship between the two sets of definition are defined as follows:

$$w_{AlI} + w_{Al2} = x\frac{W}{N} \quad (7)$$

$$w_{Ga} = (1-x)\frac{W}{N} \quad (8)$$

$$t_1 = \frac{w_{AlI}}{r_{Al}} \quad (9)$$

$$t_2 = \frac{w_{Ga}}{r_{Ga}} = \frac{w_{Al2}}{r_{Al}} \quad (10)$$

This gives the following solutions for $w_{AlI}$, and $t_2$:

$$w_{AlI} = \frac{W}{N}\left[x - (1-x)\frac{r_{Al}}{r_{Ga}}\right], \quad (11)$$

$$t_2 = \frac{W(1-x)}{Nr_{Ga}}. \quad (12)$$

In this scheme, the duration, $t_2$, of the Ga pulses are precalcualted by the controller 124 according to the above equation (12). Likewise, the N+1 integrated Al and Ga thickness set points, the Wk terms (where k=0 to N), in monolayers are precalculated according to equation (13) below:

$$w_k = \begin{cases} \frac{1}{2}w_{AlI}, & \text{for } k = 0 \\ \frac{1}{2}w_{AlI} + \frac{k}{N}w, & \text{for } k = 1, 2, ..., N-2, N-1 \\ w, & \text{for } k = N \end{cases} \quad (13)$$

During the deposition process, the controller 124 continually compares the combined integrated thicknesses of Al and Ga to $w_k$ for determining whether to initiate the deposition f Ga. The thicknesses are determined by integrating both Al and Ga atomic absorption. During the time when Ga is being deposited the controller 124 waits for time $t_2$ to pass and then it closes molecular beam shutter 66b thus ending the Ga pulse and thereby causing the deposition as shown in FIG. 17.

Cascaded PID Controller

It has been discovered that a cascaded PID controller can be used to more accurately track the desired flux of material being released by a source. For example, when the sources are solid sources the group III atomic fluxes are produced by heating material in an effusion cell which consists of a heated ceramic crucible inside the vacuum chamber. The temperature of the effusion cell is conventionally regulated with a thermocouple and a standard PID control loop. In general, a higher temperature causes more flux of material to be emitted from the effusion cell than a lower temperature. The problem with the prior art method is that the thermocouple does not measure the true temperature of the material in the crucible. Furthermore, even if the true temperature of the material remains constant, the amount of the flux of material can change as the level of material in the effusion cell recedes.

The OFM can be used to monitor the output of the effusion cells by measuring the flux of material as described above. This information can then be used to control the heating of the effusion cells to maintain a constant flux, or to create a controlled variation in the flux. Since the direct output of the cells is being measured, the inaccuracy of the thermocouple sensor is no longer important.

Figure 18:
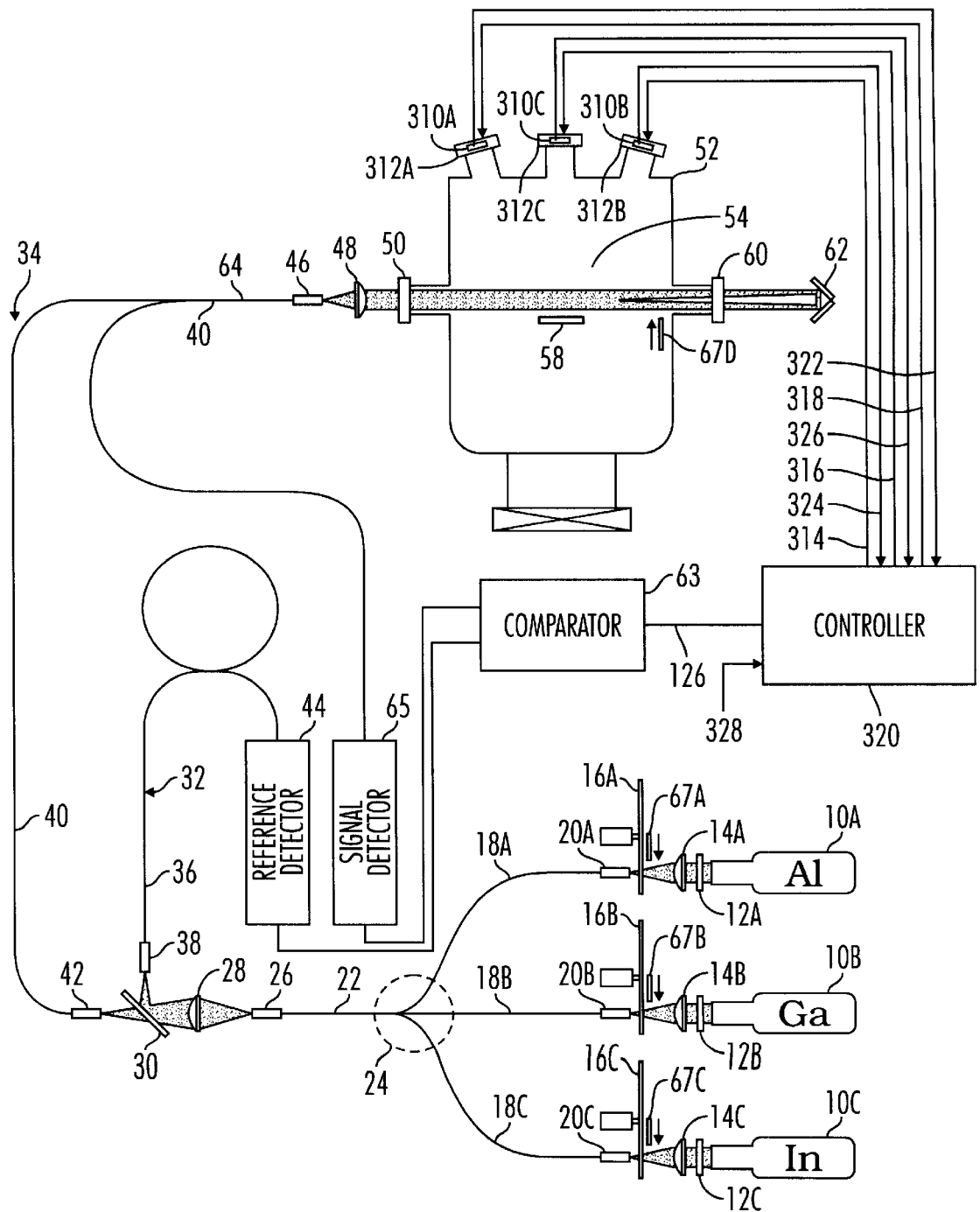
FIG. 18 is a schematic diagram of the first embodiment of the invention including a cascaded PID controller and effusion cell sources.

FIG. 18 illustrates the OFM of this invention including the use of three thermocouples 310a–c and a controller 320 that utilizes a cascaded PID controller setup. The thermocouples 310a–c are placed in proximate relationship with the effusion cells 312a–c. The lines 314, 316 and 318 carry the control signal from the controller 320 to the effusion cells 312a–c. The lines 322, 324 and 326 carry the output of the thermocouples 310a–c, respectively, to the controller 320. The desired flux setpoint (e.g., the desired composition and thickness of the deposited film on the substrate 58) is entered into the controller 320 at 328.

Figure 19:
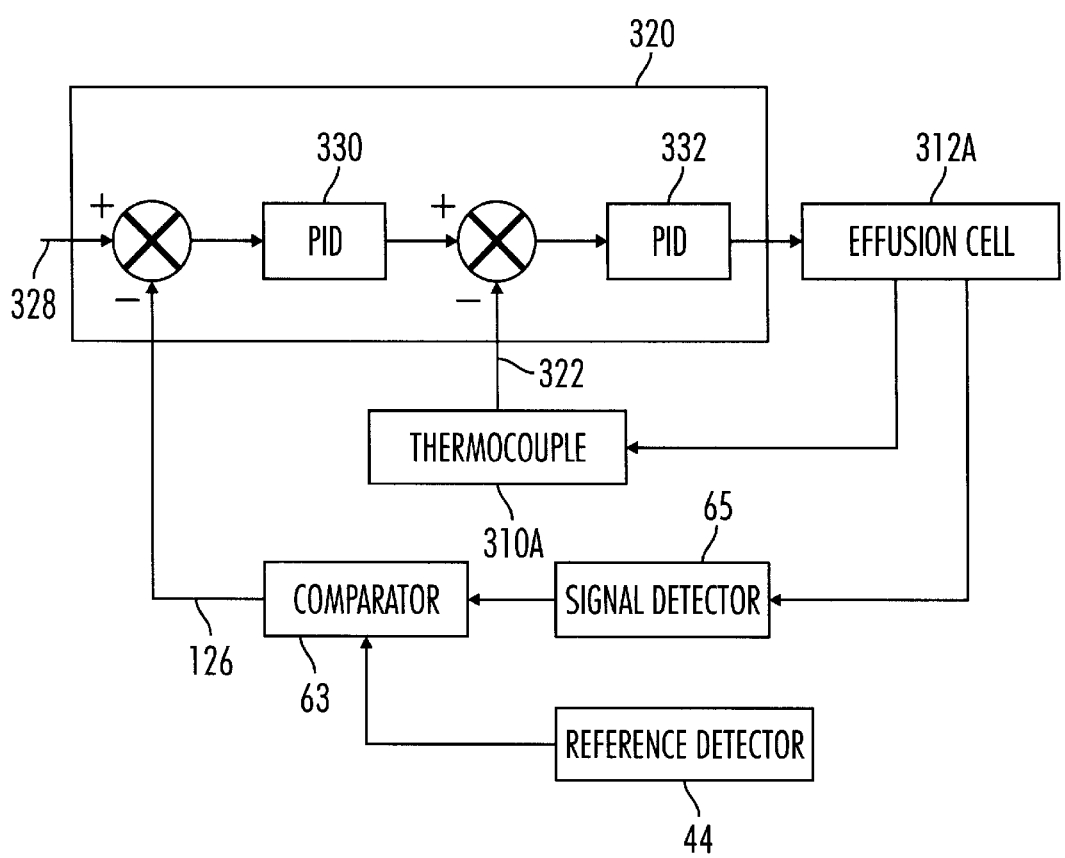
FIG. 19 is a schematic diagram of a cascaded PID controller of this invention.

The effusion cells are controlled using the OFM in a cascade configuration as shown in FIG. 19. FIG. 19 illustrates the cascade configuration for only one channel. For a three channel OFM there would be three such configurations. There are two separate PID control loops nested within each other. The outer loop is the master loop and it compares the measured flux with the desired flux and makes corrections by changing the setpoint in the inner loop which is the slave loop. The slave loop controls the heater and uses the thermocouple as feedback.

Specifically, the controller 320 includes a first PID controller 330 and a second PID controller 332. The first PID controller 330 receives the difference between the desired flux setpoint 328 entered by the user and the signal 126 from the comparator 63. The difference between the output from the first PID controller 330 and the output of the thermocouple 310a is input to the second PID controller 332. The output of the second PID controller 332 controls the effusion cell 312a by either causing the effusion cell to heat more, less or the same. If for example, the effusion cell is heated to a higher temperature, then the result is an increase in the flux of material. The increase in the flux of material is detected via the increased atomic absorption and the appropriate signal fed back to the controller 124 from the detectors 44 and 65 and the comparator 63 through line 126. The additional heat in the effusion cell 312a is also measured by the thermocouple 310a which inputs its measurement to the controller 320 through line 322 wherein the control loop starts over.

Figure 20:
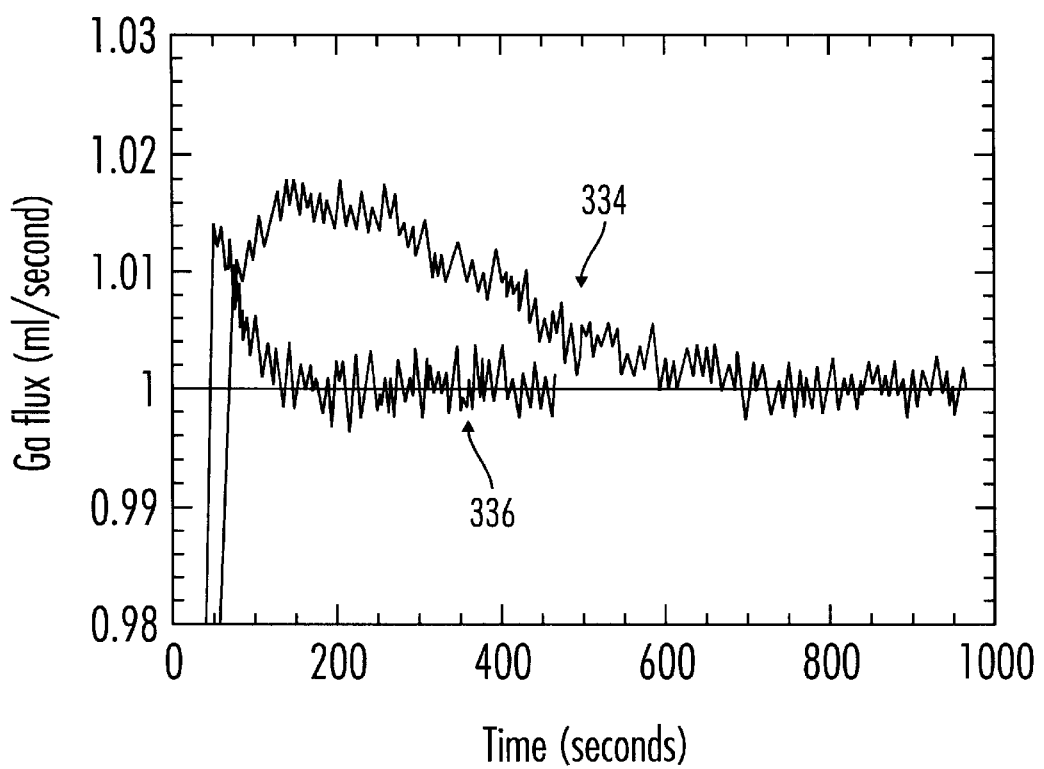
FIG. 20 is a graph showing the step response of the deposition of Gallium with and without a cascaded PID controller.

FIG. 20 is a graph of experimental results comparing the step response using only thermocouple control to the step response using OFM control with a cascaded PID controller. The x-axis measures the time of deposition of Gallium in seconds and the y-axis measures the rate of deposition of Gallium in ML/second (monolayers per second). The desired flux is 1.00 ML/second which is represented by the solid line and the starting flux rate (at time=0.0 seconds) is 0.6 ML/second. The thermocouple control is shown by reference number 334. The OFM control is represented by reference number 336. It can be seen from this graph that the OFM control method achieves the desired flux rate faster than the thermocouple only control method.

Certifying Deposition Attributes

Figure 21:
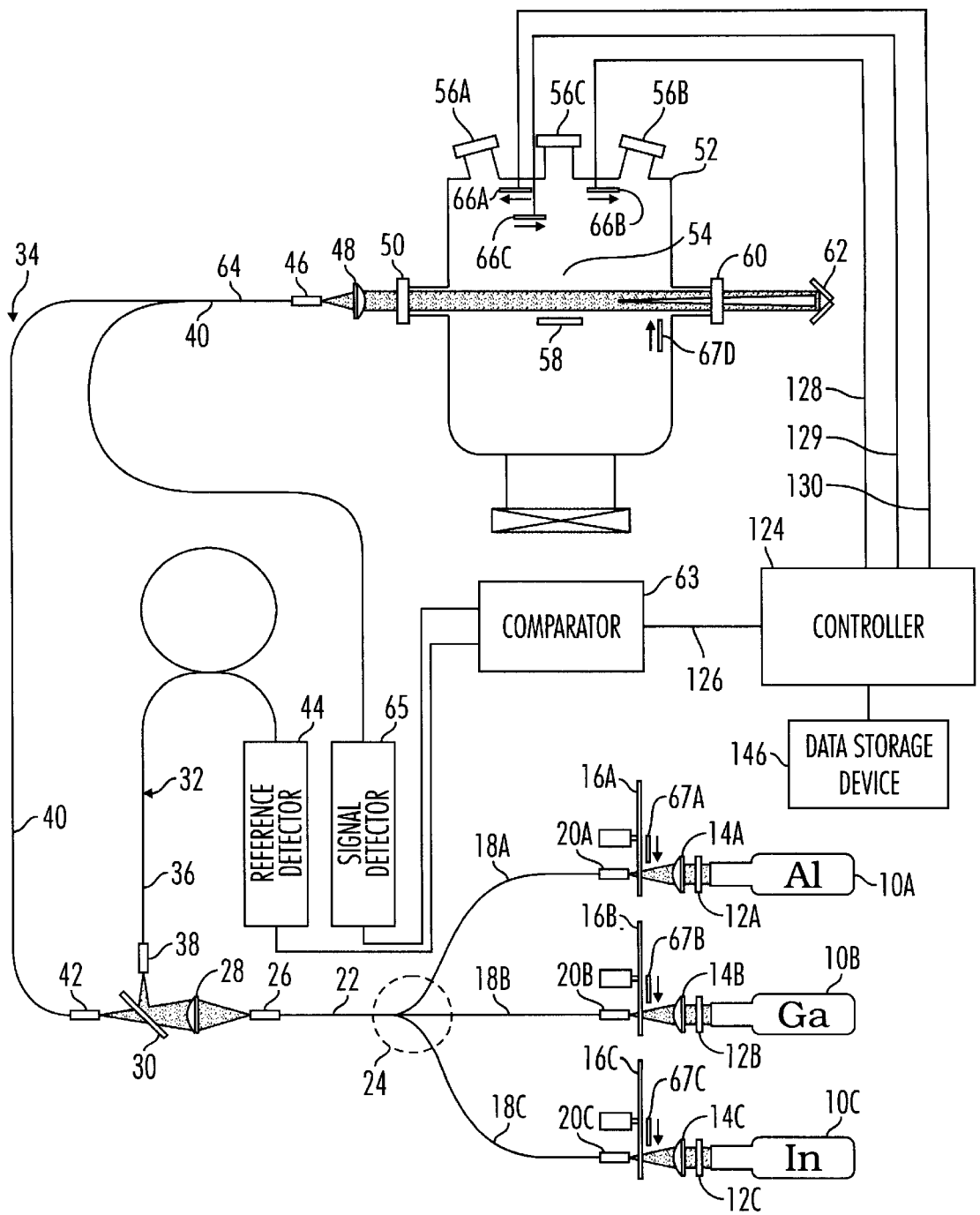
FIG. 21 is a block diagram of the present invention including a data storage device.

FIG. 21 shows a data storage device 146, wherein the deposition attributes monitored by atomic absorption are stored as certification data in a certification data structure. The data storage device 146 can be any memory such as a disk drive, floppy disk, tape or any other device for storage of data. The data storage device 146 is electrically connected to the controller 124 and the controller 124 writes the deposition attributes such as deposition thickness and composition to the data storage device 146. In an alternate embodiment, without a controller 124, the data storage device 146 can be electrically connected to the comparator 63 in the first embodiment or to the detectors 80a–c in the second embodiment, which then write the deposition attributes to the data storage device 146.

The certification data written by the controller 146 onto the data storage device 146 can be accessed by an application program executed by a data processing system. The application program can organize and display the certification data of a given deposition. The certification data is useful for certification (e.g., documentation) of the resulting article of manufacture such as the quantum well or ternary digital alloy superlattice, for example. The certification data is also useful for certification and record keeping of the deposition process and history (e.g., deposition rates within the vacuum chamber over time).

Atomic Absorption to Monitor Multi-Component Re-Evaporation

Another use of the integrated multi-channel flux monitor is for measuring the re-evaporation from the substrate 58 to determine the composition and thickness of the film on the substrate. Frequently such attributes of a film on a substrate are not known, for whatever reason, and therefore it is desirable to have a method of determining the attributes.

The present invention provides a device for measuring the attributes, such as thickness and composition of a multi-component film on a substrate by atomic absorption. It is noted that this is a destructive test because the film is removed from the substrate in the process of measuring its attributes.

Figure 22:
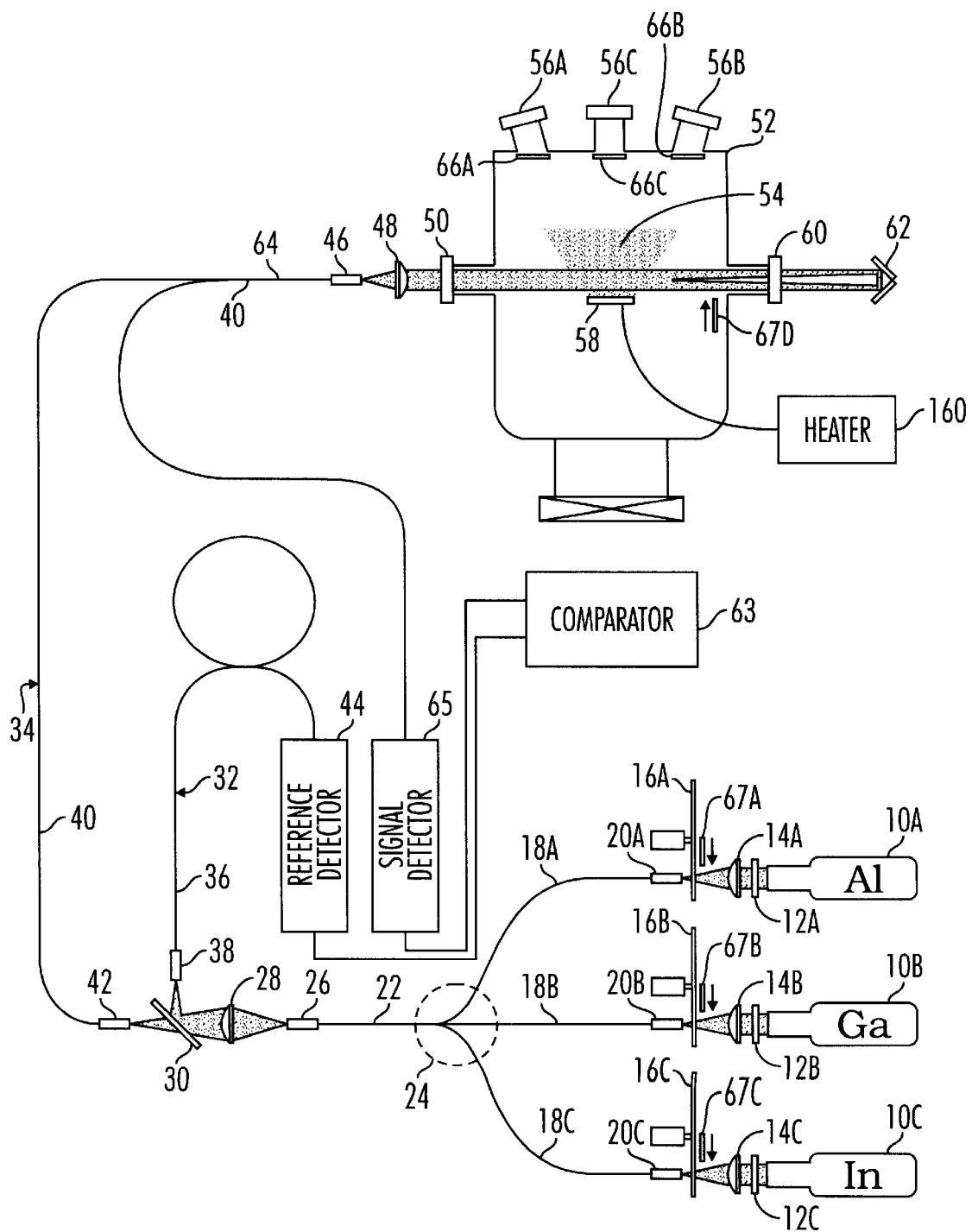
FIG. 22 is a schematic diagram of the first embodiment of this invention including a heater attached to the substrate for evaporating atomic species.

FIG. 22 shows an exemplary setup used for performing such measurements. The first step is to evaporate the atomic species from the film existing on the substrate 58. Evaporation can be achieved by heating the substrate 58 via the heater 160. As the substrate is heated, the atomic species in the film evaporate from the surface of the substrate 58. As the atomic species are ejected from the film, they enter the region 54 and pass through the combined beam of the signal arm 34. The atomic absorption is monitored as described earlier in this description, thus yielding the desired measurements of the attributes of the film as it existed before it was evaporated. The shutters 66a, 66b and 66c are closed, so that the atomic absorption measurements are not affected by atomic species originating from the sources 56a–c.

Figure 23:
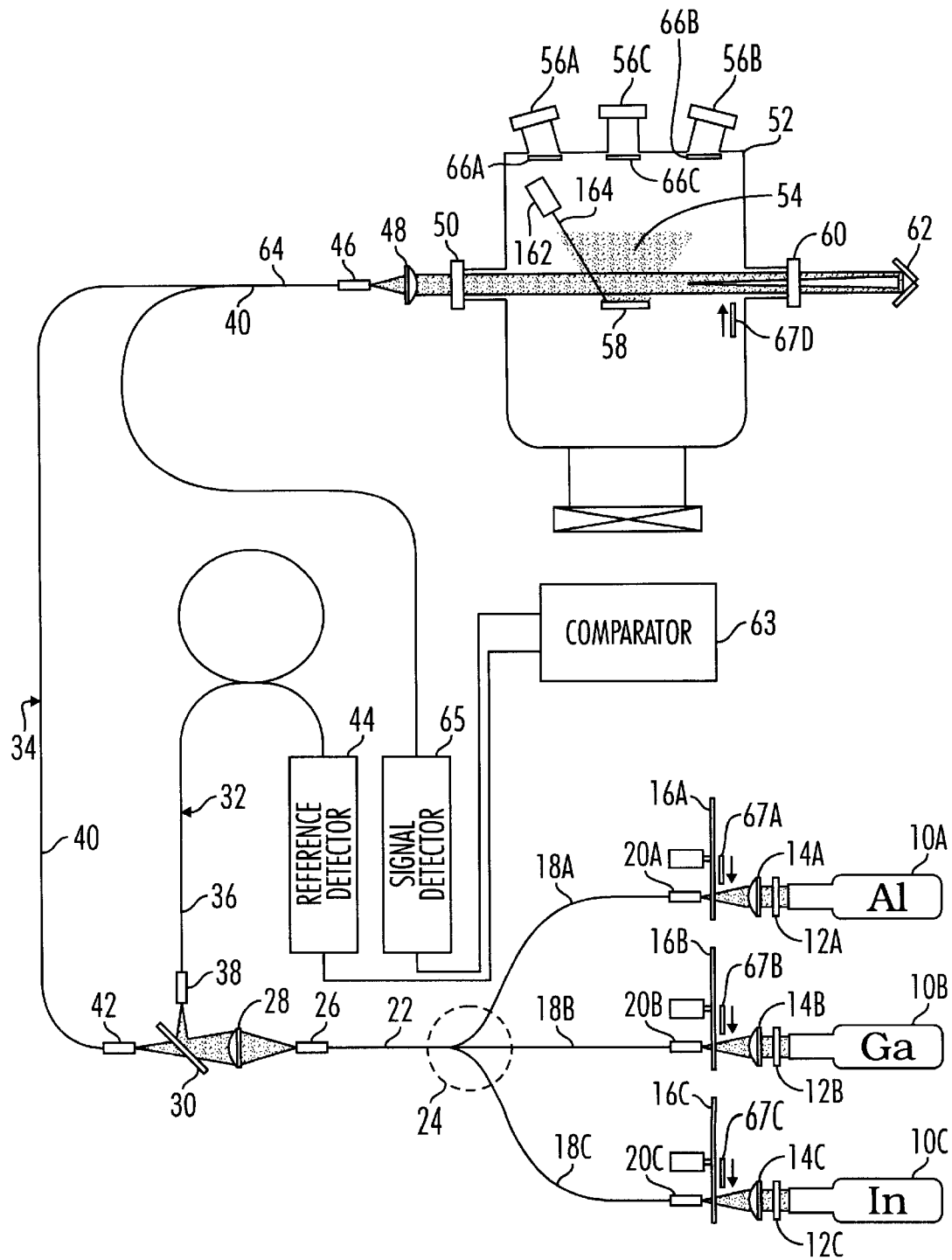
FIG. 23 is a schematic diagram of the first embodiment of the present invention including a laser gun for evaporating the atomic species from the substrate surface.

A second example of evaporation of the atomic species from the film is shown in FIG. 23. FIG. 23 illustrates the same system as shown in FIG. 22 except that the evaporation of the atomic species from the film on the substrate 58 is accomplished by laser ablation. The laser gun 162 emits light 164 which strikes the film on substrate 58. The light 164 causes the atomic species present in the film to evaporate thus passing through the region 54 and the combined beam of the signal arm 34.

While the present invention has been described in connection with the preferred embodiment thereof, it will be understood that many modifications will be readily apparent to those of ordinary skill in the art, and this application is intended to cover any adaptations or variations thereof. Therefore, it is manifestly intended that this invention be limited only by the claims and the equivalents thereof.

What is claimed is:

1. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises:

energizing a plurality of light sources so that light is emitted therefrom;

combining the light from the plurality of light sources;

splitting the combined light into a reference arm and a signal arm;

transmitting the light in the signal arm along an optical path through the flux of material in the vacuum chamber; and comparing the light in the reference arm to the light in the signal arm after the light in the signal arm has passed through the flux of material being deposited on the substrate.

2. The method of claim 1, further comprising calibrating the measurement of the atomic absorption.

3. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises:

energizing a plurality of light sources so that light is emitted therefrom;

combining the light from the plurality of light sources;

splitting the combined light into a reference arm and a signal arm;

transmitting the light in the signal arm along an optical path through the flux of material in the vacuum chamber;

comparing the light in the reference arm to the light in the signal arm after the light in the signal arm has passed through the flux of material being deposited on the substrate; and calibrating the measurement of the atomic absorption;

wherein the step of calibrating the measurement of the atomic absorption comprises:

energizing a calibration light source resulting in the emission of a calibration light, the calibration light having a wavelength such that the calibration light is not atomically absorbed by the flux of material;

combining the calibration light with the light from the plurality of light sources;

splitting the calibration light into the reference arm and the signal arm;

transmitting the calibration light in the signal arm along an optical path through the flux of material in the vacuum chamber;

measuring the intensity of the calibration light in the reference arm and the calibration light in the signal arm, after the calibration light in the signal arm has passed through the flux of material; and determining the atomic absorption from the measured intensity of the calibration light in the reference and signal arms.

4. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises the steps of:

energizing a plurality of light sources;

filtering light from each of the light sources through a plurality of bandpass filters, the output of each bandpass filter being a bandpass output;

modulating the bandpass outputs;

combining the bandpass outputs into a combined beam in one optical fiber;

splitting the light of the combined beam into a reference arm and a signal arm;

producing a plurality of reference signals such that each reference signal corresponds to a bandpass output from the reference arm, wherein the reference signal is a measure of the intensity of the corresponding bandpass output;

sending the combined beam in the signal arm through the vacuum chamber wherein the combined beam in the signal arm passes through a region between a source and the substrate thereby passing through the flux of material;

producing a plurality of probe signals such that each probe signal corresponds to a bandpass output from the signal arm, wherein the probe signal is a measure of the intensity of the corresponding bandpass output after the bandpass output has passed through the region; and comparing the reference signals to the probe signals to determine the atomic absorption of the plurality of atomic species in the flux of material.

5. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises the steps of:

energizing a plurality of light sources to emit light beams of different wavelengths;

splitting the light beam from each light source into a reference arm and a signal arm, such that there are at least two reference arms and at least two signal arms and each reference arm has a corresponding signal arm;

multiplexing the light beams in the signal arms to share an optical path that passes through the flux of material in the vacuum chamber;

demultiplexing the multiplexed light beams after they have passed through the flux of material; and comparing the light beams in the reference arm to the demultiplexed light beams to determine atomic absorption of the light beams by the plurality of atomic species in the flux of material.

6. The method of claim 5, wherein the monitoring step further comprises calibrating the measurement of the atomic absorption.

7. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises the steps of:

energizing a plurality of light sources to emit light beams of different wavelengths;

splitting the light beam from each light source into a reference arm and a signal arm, such that there are at least two reference arms and at least two signal arms and each reference arm has a corresponding signal arm;

multiplexing the light beams in the signal arms to share an optical path that passes through the flux of material in the vacuum chamber;

demultiplexing the multiplexed light beams after they have passed through the flux of material; and comparing the light beams in the reference arm to the demultiplexed light beams to determine atomic absorption of the light beams by the plurality of atomic species in the flux of material;

wherein the monitoring step further comprises calibrating the measurement of the atomic absorption; and wherein the calibrating step further comprises:

energizing a plurality of calibration light sources resulting in the emission of a plurality of calibration lights, the calibration lights having a wavelength such that the calibration lights are not atomically absorbed by the flux of material;

splitting each of the plurality of calibration light sources into a reference arm and a signal arm, each of the plurality of calibration lights being transmitted with one of the plurality of light beams wherein each of the plurality of light beams has a corresponding calibration light measuring the intensity of the calibration light in one or more of the reference arms and in one or more of the signal arms after the calibration light in the signal arms has passed through the flux of material; and determining the atomic absorption from the measured intensity of the calibration light in the one or more signal arms and the one or more reference arms.

8. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises the steps of:

energizing a plurality of light sources to generate light therefrom;

splitting the light from the light sources into a plurality of reference arms and a plurality of signal arms, wherein there is one reference arm and one signal arm corresponding to each light source;

modulating the light in each of the reference arms;

modulating the light in each of the signal arms;

producing a plurality of reference signals wherein each reference signal is proportional to the intensity of the light from a reference arm;

sending the light from the signal arm through the vacuum chamber wherein the light from the signal arm passes through a region between a source and the substrate thereby passing through the flux of material;

capturing the light from the signal arm in an optic fiber;

producing a plurality of probe signals wherein each probe signal is proportional to the intensity of light in a signal arm; and comparing the reference signals to the probe signals to determine the atomic absorption of the plurality of atomic species in the flux of material.

9. A method of controlling an epitaxial deposition of a flux of material deposited on a substrate in a vacuum chamber, comprising the steps of:

depositing the flux of material on the substrate in the vacuum chamber;

monitoring the depositing step by measuring atomic absorption by a plurality of atomic species in the flux of material; and modifying the depositing step in response to the measured atomic absorption to control the epitaxial deposition of the flux of material deposited on the substrate;

wherein the monitoring step comprises the step of determining a deposition attribute for each of the plurality of atomic species in the flux of material.

10. The method of claim 9, wherein the deposition attribute comprises a composition of the plurality of atomic species in the flux of material.

11. An apparatus for controlling the deposition of a plurality of atomic species onto a substrate in a vacuum chamber comprising:

means for depositing a plurality of atomic species onto the substrate to form a film having deposition attributes;

means for monitoring the deposition attributes of the deposition of a plurality of atomic species onto a substrate and for outputting an electrical attribute signal carrying the deposition attributes; and means for modifying the means for depositing, wherein the means for modifying receives the attribute signal from the means for monitoring and sends an electrical control signal to the means for depositing, wherein the deposition of the plurality of atomic species is modified in response to the electrical control signal;

wherein the depositing means comprises a vacuum chamber, the vacuum chamber comprising a plurality of sources and a first port;

wherein the monitoring means comprises:

a plurality of light sources;

means for combining the light from the light sources into a combined beam in a single optical fiber;

a beam splitter for splitting the combined beam into a reference arm and a signal arm, wherein the signal arm is aligned with the first port of the vacuum chamber and the light in the signal arm passes through the first port and through a region between the sources and the substrate, and wherein the material deposited on the substrate has deposition attributes;

a first detector for receiving the light in the reference arm, and producing a plurality of reference signals in response thereto;

a second detector for receiving the light in the signal arm after the light in the signal arm passes through a flux of material in the region between the source and the substrate, the second detector producing a plurality of probe signals in response thereto;

means for comparing the plurality of probe signals to the plurality of reference signals to determine the atomic absorption of the plurality of atomic species and for outputting an electrical attribute signal, wherein the electrical attribute signal contains information about the atomic absorption of the plurality of atomic species.

12. The apparatus of claim 11, wherein the monitoring means further comprises means for calibrating the comparing means.

13. The apparatus of claim 11, wherein the means for modifying the means for depositing comprises means for modifying the vacuum chamber, the modifying means being electrically connected to the comparing means and the modifying means connected to the plurality of sources, wherein the modifying means modifies the vacuum chamber in response to the electrical attribute signal received from the means for comparing, wherein the modification results in a change in the deposition attributes of the material being deposited.

14. The apparatus of claim 13, wherein the plurality of sources are effusion cells.

15. The apparatus of claim 11, wherein the reference signals are equal to a signal measured when the light in the reference arm is not blocked from passing through the reference arm minus a signal measured when the light in the reference arm is blocked from passing through the reference arm.

16. The apparatus of claim 15, wherein the means for comparing comprises:

means for measuring a probe intensity offset, R, by determining the intensity of light in the signal arm when the light in the signal arm is blocked from passing through the signal arm and dividing the determined intensity by the reference signal;

means for measuring a transmitted probe intensity, $T_0$, by determining the intensity of light in the signal arm when the flux of material is blocked from striking the substrate and the light in the signal arm is not blocked from passing through the signal arm and dividing the determined intensity by the reference signal and subtracting the probe intensity offset, R;

means for measuring a probe intensity signal, $R+T_0-A$ by determining the intensity of light in the signal arm when the flux of material is not blocked from striking the substrate and the light in the signal arm is not blocked from passing through the signal arm and dividing the determined intensity by the reference signal; and means for calculating a normalized absorption, g, using the probe intensity offset, transmitted probe intensity and probe intensity signal according to the relationship $$\gamma = A/T_0.$$

17. The apparatus of claim 11, wherein the light sources comprise three light sources.

18. The apparatus of claim 17, wherein the means for combining comprises a trifurcating optical fiber bundle.

19. The apparatus of claim 11, wherein the vacuum chamber further comprises a second port, wherein the light from the signal arm enters the vacuum chamber via the first port and exits the vacuum chamber via the second port.

20. The apparatus of claim 19, further including a retroreflector positioned outside the second port of the vacuum chamber, wherein the light from the signal arm, after exiting the vacuum chamber through the second port, is retroreflected into the vacuum chamber via the second port and then exits the vacuum chamber via the first port, thereby completing two passes through the region between the source and the substrate.

21. The apparatus of claim 19, wherein the first and second ports each comprise a heater for maintaining a substantially constant temperature of the respective first and second ports to substantially eliminate coating of the respective first and second ports during the epitaxial process.

22. The apparatus of claim 11, further including a retroreflector attached to the inside of the chamber, wherein the light from the signal arm is retroreflected through the vacuum chamber exiting through the first port, thereby completing two passes through the region between the source and the substrate.

23. The apparatus of claim 22, wherein the retroreflector further comprises a heater for maintaining a substantially constant temperature of the retroreflector to substantially eliminate coating of the retroreflector during the epitaxial process.

24. The apparatus of claim 11, wherein the first detector comprises:
a collimating lens wherein the light entering the detector passes through the collimating lens;
a filter aligned with the collimating lens such that the light entering the detector and passing through the collimating lens passes into the filter;
a photomultiplier tube aligned with the filter such that the light exiting the filter strikes the photomultiplier tube, the photomultiplier tube having an electrical output; and
a plurality of lock-in amplifiers electrically connected to the output of the photomultiplier tube.

25. The apparatus of claim 11, wherein the second detector comprises:

a collimating lens wherein the light entering the detector passes through the collimating lens;
a filter aligned with the collimating lens such that the light entering the detector and passing through the collimating lens passes into the filter;
a photomultiplier tube aligned with the filter such that the light exiting the filter strikes the photomultiplier tube, the photomultiplier tube having an electrical output; and
a plurality of lock-in amplifiers electrically connected to the output of the photomultiplier tube.

26. The apparatus of claim 11, wherein the light sources are selected from a group consisting of hollow cathode lamps, laser diodes and laser systems.

27. The apparatus of claim 11, further comprising an alignment light source injecting an alignment light into the reference arm and the signal arm such that the alignment light is combined with the combined beam, wherein the signal arm is aligned with the vacuum chamber.

28. The apparatus of claim 11, wherein the vacuum chamber further comprises a plurality of molecular beam shutters, wherein each molecular beam shutter corresponds to a source, wherein the closing of a molecular beam shutter blocks the flux of the atomic species originating from the corresponding source from reaching the substrate; and wherein means for modifying comprises a controller electrically connected to two or more of said molecular beam shutters such that said controller causes said molecular beam shutters to move, thereby changing the amount of flux of atomic species from the corresponding sources.

29. The apparatus of claim 14, wherein the vacuum chamber further comprises a plurality of temperature sensors, one temperature sensor proximate to each effusion cell wherein each temperature sensor sends an output signal to the modifying means.

30. The apparatus of claim 29, wherein the modifying means further comprises a cascading PID controller.

31. An apparatus for controlling the deposition of a plurality of atomic species onto a substrate in a vacuum chamber comprising:

means for depositing a plurality of atomic species onto the substrate to form a film having deposition attributes;

means for monitoring the deposition attributes of the deposition of a plurality of atomic species onto a substrate and for outputting an electrical attribute signal carrying the deposition attributes; and means for modifying the means for depositing, wherein the means for modifying receives the attribute signal from the means for monitoring and sends an electrical control signal to the means for depositing, wherein the deposition of the plurality of atomic species is modified in response to the electrical control signal;

wherein the depositing means comprises a vacuum chamber, the vacuum chamber comprising a plurality of sources and a first port; and wherein the monitoring means comprises:
a plurality of light sources;
means for combining the light from the light sources into a combined beam in a single optical fiber;
a beam splitter for splitting the combined beam into a reference arm and a signal arm, wherein the signal arm is aligned with the first port of the vacuum chamber and the light in the signal arm passes through the first port and through a region between the sources and the substrate, and wherein the material deposited on the substrate has deposition attributes;

a first detector for receiving the light in the reference arm, and producing a plurality of reference signals in response thereto;

a second detector for receiving the light in the signal arm after the light in the signal arm passes through a flux of material in the region between the source and the substrate, the second detector producing a plurality of probe signals in response thereto;

means for comparing the plurality of probe signals to the plurality of reference signals to determine the atomic absorption of the plurality of atomic species and for outputting an electrical attribute signal, wherein the electrical attribute signal contains information about the atomic absorption of the plurality of atomic species;

wherein the monitoring means further comprises means for calibrating the comparing means; and wherein calibrating means comprises:

a calibration light source which when energized produces a calibration light, the calibration light having a wavelength such that the calibration light is not atomically absorbed by the flux of material, wherein part of the calibration light is transmitted along the reference arm and part of the calibration light is transmitted along the signal arm; and means for comparing the calibration light in the reference arm to the calibration light in the signal arm, and changing the attribute signal based on the comparison.

32. An apparatus for controlling the deposition of a plurality of atomic species onto a substrate in a vacuum chamber comprising:

means for depositing a plurality of atomic species onto the substrate to form a film having deposition attributes;

means for monitoring the deposition attributes of the deposition of a plurality of atomic species onto a substrate and for outputting an electrical attribute signal carrying the deposition attributes; and means for modifying the means for depositing, wherein the means for modifying receives the attribute signal from the means for monitoring and sends an electrical control signal to the means for depositing, wherein the deposition of the plurality of atomic species is modified in response to the electrical control signal;

wherein the depositing means comprises a vacuum chamber, the vacuum chamber comprising a plurality of sources and a first port;

wherein the monitoring means comprises:

a plurality of light sources emitting light;

a beam splitter for splitting the light into a plurality of reference arms and a plurality of signal arms, wherein there is one reference arm and one signal arm corresponding to each light source, wherein the plurality of signal arms are aligned with the first port and the light in the signal arms passes through the first port and through a region between the source and the substrate, said substrate being contained within the vacuum chamber and wherein the material deposited on the substrate has deposition attributes;

a plurality of detectors for receiving the light from the reference arms and the signal arms, and producing a plurality of reference signals and a plurality of probe signals in response thereto; and means for comparing the probe signals to the reference signals to determine the atomic absorption of the atomic species, wherein each reference signal corresponds to the intensity of light in a reference arm and each probe signal corresponds to the intensity of light in a signal arm, and the comparing means for outputting an electrical attribute signal, wherein the electrical attribute signal contains information about the atomic absorption of the plurality of atomic species.

33. The apparatus of claim 32, further comprising means for calibrating the comparing means.

34. The apparatus of claim 32, wherein the means for modifying the means for depositing comprises means for modifying the vacuum chamber, modifying means being electrically connected to the comparing means and connected to the vacuum chamber, wherein the modifying means modifies the vacuum chamber in response to the electrical attribute signal received from comparing means, wherein the modification results in a change in the deposition attributes of the material being deposited.

35. The apparatus of claim 34, wherein the comparing means comprises:

means for measuring a probe intensity offset, R, by determining the intensity of light in the signal arm when the light in the signal arm is blocked from passing through the signal arm and dividing the determined intensity by the reference signal;

means for measuring a transmitted probe intensity, To, by determining the intensity of light in the signal arm when the flux of material is blocked from striking the substrate and the light in the signal arm is not blocked from passing through the signal arm and dividing the determined intensity by the reference signal and subtracting the probe intensity offset, R;

means for measuring a probe intensity signal, $R+T_0-A$ by determining the intensity of light in the signal arm when the flux of material is not blocked from striking the substrate and the light in the signal arm is not blocked from passing through the signal arm and dividing the determined intensity by the reference signal; and means for calculating a normalized absorption, g, using the probe intensity offset, transmitted probe intensity and probe intensity signal according to the relationship $\gamma = A/T_0$.

36. The apparatus of claim 32, wherein the light sources comprise three light sources.

37. The apparatus of claim 32, wherein the vacuum chamber further includes a second port such that the light from the signal arm enters the vacuum chamber through the first port and exits the vacuum chamber through the second port.

38. The apparatus of claim 37, further including a retroreflector positioned outside the second port of the vacuum chamber wherein the light from the signal arm, after exiting the vacuum chamber via the second port, is retroreflected into the vacuum chamber via the second port and then exits the vacuum chamber via the first port, thereby completing two passes through the region between the source and the substrate.

39. The apparatus of claim 37, wherein the first and second ports each include a heater for maintaining a substantially constant temperature of the respective first and second ports to substantially eliminate coating of the respective first and second ports during the epitaxial process.

40. The apparatus of claim 39, wherein the retroreflector further comprises a heater for maintaining a substantially constant temperature of the retroreflector to substantially eliminate coating of the retroreflector during the epitaxial process.

41. The apparatus of claim 32, further including a retroreflector attached to the inside of the chamber wherein the light from the signal arm is retroreflected through the vacuum chamber, exiting through the first port, and thereby completing two passes through the region between the source and the substrate.

42. The apparatus of claim 32, wherein each detectors comprises:
   a collimating lens wherein the light entering the detector passes through the collimating lens;
   a filter aligned with the collimating lens wherein the light entering the detector passes into the filter;
   a photomultiplier tube aligned with the filter wherein the light exiting the filter strikes the photomultiplier tube, the photomultiplier tube having an electrical output; and
   a plurality of lock-in amplifiers electrically connected to the output of the photomultiplier tube.

43. The apparatus of claim 32, wherein the light sources are selected from a group consisting of hollow cathode lamps, laser diodes and laser systems.

44. The apparatus of claim 32, further comprising an alignment light source injecting an alignment light into the signal arm wherein the signal arm is aligned with the vacuum chamber.

45. An apparatus for controlling the deposition of a plurality of atomic species onto a substrate in a vacuum chamber comprising:
   means for depositing a plurality of atomic species onto the substrate to form a film having deposition attributes;
   means for monitoring the deposition attributes of the deposition of a plurality of atomic species onto a substrate and for outputting an electrical attribute signal carrying the deposition attributes; and
   means for modifying the means for depositing, wherein the means for modifying receives the attribute signal from the means for monitoring and sends an electrical control signal to the means for depositing, wherein the deposition of the plurality of atomic species is modified in response to the electrical control signal;
   wherein the depositing means comprises a vacuum chamber, the vacuum chamber comprising a plurality of sources and a first port;
   wherein the monitoring means comprises:
      a plurality of light sources emitting light;
      a beam splitter for splitting the light into a plurality of reference arms and a plurality of signal arms, wherein there is one reference arm and one signal arm corresponding to each light source, wherein the plurality of signal arms are aligned with the first port and the light in the signal arms passes through the first port and through a region between the source and the substrate, said substrate being contained within the vacuum chamber and wherein the material deposited on the substrate has deposition attributes;
      a plurality of detectors for receiving the light from the reference arms and the signal arms, and producing a plurality of reference signals and a plurality of probe signals in response thereto; and
      means for comparing the probe signals to the reference signals to determine the atomic absorption of the atomic species, wherein each reference signal corresponds to the intensity of light in a reference arm and each probe signal corresponds to the intensity of light in a signal arm, and the comparing means for outputting an electrical attribute signal, wherein the electrical attribute signal contains information about the atomic absorption of the plurality of atomic species; and
   means for calibrating the comparing means;
   wherein the means for calibrating comprises:
      a plurality of calibration light sources which when energized each produce a calibration light, the calibration light having a wavelength such that the calibration light is not atomically absorbed by the flux of material, wherein each calibration light source transmits a calibration light along the reference arm and the signal arm of a corresponding one of the plurality of light sources; and
      means for comparing the calibration light in the reference arm to the calibration light in the signal arm, and changing the attribute signal based on the comparison.

46. A device having epitaxial layers manufactured according to the following steps:
   placing a substrate in a vacuum chamber;
   generating a flux of material from a plurality of sources;
   forming an epitaxial layer on the substrate from the flux of material;
   transmitting a plurality of light beams through the flux of material, wherein the light beams are multiplexed;
   measuring an atomic absorption of the light beams by the flux of material; and
   modifying the flux of material in accordance with the measured atomic absorption so that a desired rate of formation of the epitaxial layers is achieved.

47. The device of claim 46, wherein the modifying step comprises at least partially blocking the flux of material from at least two sources from being deposited on the substrate.

48. A method of controlling an epitaxial deposition of a flux of material deposited on a substrate in a vacuum chamber, comprising the steps of:
   depositing the flux of material on the substrate in the vacuum chamber;
   monitoring the depositing step by measuring atomic absorption by a plurality of atomic species in the flux of material; and
   modifying the depositing step in response to the measured atomic absorption to control the epitaxial deposition of the flux of material deposited on the substrate;
   wherein the depositing step comprises the step of creating a ternary quantum well at a specified deposition rate, wherein the ternary quantum well is comprised of at least three atomic species.

49. The method of claim 48, wherein the monitoring step comprises the step of monitoring the atomic absorption of at least two of the atomic species to determine one or more deposition attributes thereof.

50. The method of claim 49, wherein the modifying step comprises the steps of:
   calculating a photoluminescence peak energy of the ternary quantum well based on a model relating the deposition attributes to the photoluminescence peak energy;
   comparing the photoluminescence peak energy of the ternary quantum well to a predetermined energy set-point; and
   terminating the creating step in response to the comparison, so that the photoluminescence peak energy of the ternary quantum well is substantially the same as the predetermined energy set-point.

51. The method of claim 50, wherein the three atomic species comprise In, Ga, and As, such that the ternary quantum well comprises $In_xGa_{1-x}As$, wherein x is an average mole fraction of In.

52. The method of claim 51, wherein the model comprises a mathematical relation:

$$E(x, w) = A + B \cdot x + (C + D \cdot x)\exp\left(\frac{-w}{E + F \cdot x}\right)$$

wherein A, B, C, D, E, and F are coefficients determined experimentally and w is a width of the ternary quantum well.

53. A method of controlling an epitaxial deposition of a flux of material deposited on a substrate in a vacuum chamber, comprising the steps of:
   depositing the flux of material on the substrate in the vacuum chamber;
   monitoring the depositing step by measuring atomic absorption by a plurality of atomic species in the flux of material; and
   modifying the depositing step in response to the measured atomic absorption to control the epitaxial deposition of the flux of material deposited on the substrate;
   wherein the depositing step comprises the step of creating a ternary digital alloy superlattice.

54. The method of claim 53, wherein the depositing step comprises the step of depositing a first and a second atomic species on the substrate substantially simultaneously to form a film having an integrated thickness.

55. The method of claim 54, wherein the monitoring step comprises the step of measuring the integrated thickness of the film.

56. The method of claim 55, wherein the modifying step comprises the step of initiating the deposition of the second atomic species each time the integrated thickness of the film equals one of a plurality of set-points.

57. The method of claim 54, wherein the first atomic species is Al and the second atomic species is Ga.

58. A method of controlling an epitaxial deposition of a flux of material deposited on a substrate in a vacuum chamber, comprising the steps of:
   depositing the flux of material on the substrate in the vacuum chamber;
   monitoring the depositing step by measuring atomic absorption by a plurality of atomic species in the flux of material; and
   modifying the depositing step in response to the measured atomic absorption to control the epitaxial deposition of the flux of material deposited on the substrate;
   wherein the flux of material is derived from the heating of an effusion cell, and
   wherein the effusion cell receives an input and provides an output, the output in the form of heat energy and wherein there is a temperature sensor near the effusion cell, the temperature sensor having an output reflecting the temperature of the space near the sensor, and wherein there is a desired flux of material to be applied to the substrate, wherein the modifying step comprises:
   applying a signal representing the desired flux of material to a first input of a cascaded PID controller;
   applying a signal representing the measured atomic absorption to a second input of the cascaded PID controller;
   applying a signal from the output of the temperature sensor to a third input of the cascaded PID controller, wherein the cascaded PID controller produces an output signal based on the signals applied to the first, second and third inputs of the cascaded PID controller; and
   applying the cascaded PID controller output signal to the input of the effusion cell, wherein the heat produced by the effusion cell is dependent upon the cascaded PID controller output signal.

59. The method of claim 58 wherein the cascaded PID controller comprises a master loop and a slave loop wherein the first and second inputs to the cascaded PID controller are inputs to the master loop and the third input to the cascaded PID controller is an input to the slave loop.

* * * * *